US012611130B2

(12) United States Patent
Kelly et al.

(10) Patent No.: US 12,611,130 B2
(45) Date of Patent: Apr. 28, 2026

(54) SELF-LEARNING AND NON-INVASIVE BLADDER MONITORING SYSTEMS AND METHODS

(71) Applicant: C. R. Bard, Inc., Franklin Lakes, NJ (US)

(72) Inventors: Timothy J. Kelly, Atlanta, GA (US);
Eric A. Fallows, Apex, NC (US);
Robert Cancelosi, Tigard, OR (US);
Damien Marechal, Claix (FR);
Yolanda Rhodes, Cypress, TX (US);
Gregory Mann, Mcdonough, GA (US);
Alexandra A. Falis, Marietta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 92 days.

(21) Appl. No.: 18/278,167

(22) PCT Filed: Feb. 23, 2022

(86) PCT No.: PCT/US2022/017574
§ 371 (c)(1),
(2) Date: Aug. 21, 2023

(87) PCT Pub. No.: WO2022/182794
PCT Pub. Date: Sep. 1, 2022

(65) Prior Publication Data
US 2024/0081708 A1      Mar. 14, 2024

Related U.S. Application Data

(60) Provisional application No. 63/157,530, filed on Mar. 5, 2021, provisional application No. 63/152,715, filed
(Continued)

(51) Int. Cl.
*A61B 5/00* (2006.01)
*A61B 5/0537* (2021.01)
(Continued)

(52) U.S. Cl.
CPC ............ *A61B 5/204* (2013.01); *A61B 5/0004* (2013.01); *A61B 5/0537* (2013.01); *A61B 5/208* (2013.01);
(Continued)

(58) Field of Classification Search
CPC ....... A61B 5/204; A61B 5/391; A61B 5/0004; A61B 5/0537; A61B 5/208; A61B 5/6823;
(Continued)

(56) References Cited

U.S. PATENT DOCUMENTS 3,661,143 A    5/1972  Henkin
3,781,920 A    1/1974  Browne et al.
(Continued)

FOREIGN PATENT DOCUMENTS

CA      2882654 A1    10/2007
CN      2445749 Y      9/2001
(Continued)

OTHER PUBLICATIONS

EP 23188337.2 filed May 21, 2019 Extended European Search Report dated Dec. 4, 2023.
(Continued)

*Primary Examiner* — Joel F Brutus
(74) *Attorney, Agent, or Firm* — Rutan & Tucker LLP

(57) ABSTRACT

Embodiments disclosed herein are directed to a self-learning bladder volume monitoring system. The system can include a bladder volume (BV) system configured to measure an electrical impedance of a bladder region of a patient and determine a volume of fluid disposed therein using an impedance to bladder volume model ("By model"). Further, the system can measure a total body water ("TBW") for the patient and modify the BV model to account for variations in TBW within the tissues surrounding the bladder providing
(Continued)

a more accurate bladder volume measurement. The system can include a "training unit" which can include one of a user input interface, an automatic urine output monitoring system, an ultrasound system, and an intrabladder pressure system configured to verify a volume of fluid within or voided from the bladder and train the BV model.

25 Claims, 14 Drawing Sheets

Related U.S. Application Data on Feb. 23, 2021, provisional application No. 63/152,689, filed on Feb. 23, 2021.

(51) Int. Cl.
| | | |
|---|---|---|
| A61B 5/20 | (2006.01) | |
| A61B 5/391 | (2021.01) | |
| A61B 8/00 | (2006.01) | |
| A61B 8/08 | (2006.01) | |

(52) U.S. Cl.
CPC ............ *A61B 5/391* (2021.01); *A61B 5/6823* (2013.01); *A61B 5/6831* (2013.01); *A61B 5/721* (2013.01); *A61B 5/7267* (2013.01); *A61B 8/08* (2013.01); *A61B 8/4227* (2013.01); *A61B 8/4416* (2013.01); *A61B 8/5223* (2013.01); *A61B 2562/0219* (2013.01)

(58) Field of Classification Search
CPC ....... A61B 5/6831; A61B 8/08; A61B 8/4227; A61B 8/4416; A61B 8/5223
See application file for complete search history.

(56) References Cited

U.S. PATENT DOCUMENTS

| | | | |
|---|---|---|---|
| 3,851,650 | A | 12/1974 | Darling |
| 3,919,455 | A | 11/1975 | Sigdell et al. |
| 4,276,889 | A | 7/1981 | Kuntz et al. |
| 4,286,590 | A | 9/1981 | Murase |
| 4,291,692 | A | 9/1981 | Bowman et al. |
| 4,296,749 | A | 10/1981 | Pontifex |
| 4,305,405 | A | 12/1981 | Meisch |
| 4,312,352 | A | 1/1982 | Meisch et al. |
| 4,343,316 | A | 8/1982 | Jespersen |
| 4,443,219 | A | 4/1984 | Meisch et al. |
| 4,448,207 | A | 5/1984 | Parrish |
| 4,509,366 | A | 4/1985 | Matsushita et al. |
| 4,532,936 | A | 8/1985 | LeVeen et al. |
| 4,658,834 | A | 4/1987 | Blankenship et al. |
| 4,712,567 | A | 12/1987 | Gille et al. |
| 4,723,950 | A | 2/1988 | Lee |
| 4,834,706 | A | 5/1989 | Beck et al. |
| 4,850,375 | A | 7/1989 | Rosenberg |
| 4,889,532 | A | 12/1989 | Metz et al. |
| 5,002,541 | A | 3/1991 | Conkling et al. |
| 5,146,637 | A | 9/1992 | Bressler et al. |
| 5,409,014 | A | 4/1995 | Napoli et al. |
| 5,586,085 | A | 12/1996 | Lichte |
| 5,725,515 | A | 3/1998 | Propp |
| 5,733,319 | A | 3/1998 | Neilson et al. |
| 5,738,656 | A | 4/1998 | Wagner |
| 5,747,824 | A | 5/1998 | Jung et al. |
| 5,769,087 | A | 6/1998 | Westphal et al. |
| 5,807,278 | A | 9/1998 | McRae |
| 5,823,972 | A | 10/1998 | McRae |
| 5,891,051 | A | 4/1999 | Han et al. |
| 5,911,786 | A | 6/1999 | Nielsen et al. |
| 6,129,684 | A | 10/2000 | Sippel et al. |
| 6,132,407 | A | 10/2000 | Genese et al. |
| 6,250,152 | B1 | 6/2001 | Klein et al. |
| 6,256,532 | B1 | 7/2001 | Cha |
| 6,261,254 | B1 | 7/2001 | Baron et al. |
| 6,434,418 | B1 | 8/2002 | Neal et al. |
| 6,579,247 | B1 | 6/2003 | Abramovitch et al. |
| 6,592,612 | B1 | 7/2003 | Samson et al. |
| 6,709,420 | B1 | 3/2004 | Lincoln et al. |
| 6,716,200 | B2 | 4/2004 | Bracken et al. |
| 7,011,634 | B2 | 3/2006 | Paasch et al. |
| 7,161,484 | B2 | 1/2007 | Tsoukalis |
| 7,211,037 | B2 | 5/2007 | Briggs et al. |
| 7,437,945 | B1 | 10/2008 | Feller |
| 7,442,754 | B2 | 10/2008 | Tepper et al. |
| 7,739,907 | B2 | 6/2010 | Boiarski |
| 7,871,385 | B2 | 1/2011 | Levinson |
| 7,931,630 | B2 | 4/2011 | Nishtala et al. |
| 7,976,533 | B2 | 7/2011 | Larsson |
| 7,998,126 | B1 | 8/2011 | Fernandez |
| 8,295,933 | B2 | 10/2012 | Gerber et al. |
| 8,328,733 | B2 | 12/2012 | Forte et al. |
| 8,328,734 | B2 | 12/2012 | Salvadori et al. |
| 8,337,476 | B2 | 12/2012 | Greenwald et al. |
| 8,374,688 | B2 | 2/2013 | Libbus et al. |
| 8,403,884 | B2 | 3/2013 | Nishtala |
| 8,471,231 | B2 | 6/2013 | Paz |
| 8,663,128 | B2 | 3/2014 | Paz et al. |
| 8,773,259 | B2 | 7/2014 | Judy et al. |
| 8,790,277 | B2 | 7/2014 | Elliott et al. |
| 8,790,320 | B2 | 7/2014 | Christensen |
| 8,790,577 | B2 | 7/2014 | Mizumoto et al. |
| 8,813,551 | B2 | 8/2014 | Boiarski |
| 8,827,924 | B2 | 9/2014 | Paz et al. |
| 8,832,558 | B2 | 9/2014 | Cardarelli et al. |
| 8,900,196 | B2 | 12/2014 | Andino |
| 9,045,887 | B2 | 6/2015 | O'Malley |
| 9,050,046 | B2 | 6/2015 | Elliott et al. |
| 9,074,920 | B2 | 7/2015 | Mendels et al. |
| 9,216,242 | B2 | 12/2015 | Nishtala et al. |
| 9,480,821 | B2 | 11/2016 | Ciccone et al. |
| 9,592,034 | B2 | 3/2017 | Hall et al. |
| 9,642,987 | B2 | 5/2017 | Bierman et al. |
| 9,731,097 | B2 | 8/2017 | Andino et al. |
| 9,895,095 | B2 | 2/2018 | Chen |
| 9,928,341 | B2 | 3/2018 | Angelides |
| 9,962,516 | B2 | 5/2018 | Lampotang et al. |
| 10,071,202 | B2 | 9/2018 | Handler |
| 10,182,747 | B2 | 1/2019 | Charlez et al. |
| 10,245,008 | B2 | 4/2019 | Paige |
| 10,301,807 | B1 | 5/2019 | Kolesar |
| 10,362,981 | B2 | 7/2019 | Paz et al. |
| 10,383,606 | B1 | 8/2019 | McCord et al. |
| 10,448,875 | B2 | 10/2019 | Holt et al. |
| 10,722,679 | B2 | 7/2020 | Lampotang et al. |
| 10,799,386 | B1 | 10/2020 | Harrison, Sr. |
| 10,881,320 | B2 | 1/2021 | Duval et al. |
| 10,881,778 | B2 | 1/2021 | Scarpaci et al. |
| 11,291,577 | B2 | 4/2022 | Seres et al. |
| 11,473,958 | B2 | 10/2022 | Holt et al. |
| 11,540,760 | B1 | 1/2023 | Guillemette |
| 11,654,042 | B2 | 5/2023 | Hughett, Sr. |
| 11,703,365 | B2 | 7/2023 | Tourchak et al. |
| 12,083,261 | B2 | 9/2024 | Justice et al. |
| 12,109,353 | B2 | 10/2024 | Cheng et al. |
| 12,364,423 | B2 | 7/2025 | Cheng et al. |
| 12,408,853 | B2 | 9/2025 | Kriscovich et al. |
| 2001/0056226 | A1 | 12/2001 | Zodnik et al. |
| 2002/0016719 | A1 | 2/2002 | Nemeth et al. |
| 2002/0161314 | A1 | 10/2002 | Sarajarvi |
| 2002/0193760 | A1 | 12/2002 | Thompson |
| 2003/0000303 | A1 | 1/2003 | Livingston et al. |
| 2003/0163183 | A1 | 8/2003 | Carson |
| 2003/0163287 | A1 | 8/2003 | Vock et al. |
| 2004/0267086 | A1 | 12/2004 | Anstadt et al. |
| 2005/0020958 | A1 | 1/2005 | Paolini et al. |
| 2005/0065583 | A1 | 3/2005 | Voorhees et al. |
| 2005/0172712 | A1 | 8/2005 | Nyce |
| 2005/0247121 | A1 | 11/2005 | Pelster |
| 2006/0065713 | A1 | 3/2006 | Kingery |
| 2006/0100743 | A1 | 5/2006 | Townsend et al. |
| 2006/0253091 | A1 | 11/2006 | Vernon |
| 2007/0010797 | A1 | 1/2007 | Nishtala et al. |

(56) References Cited

U.S. PATENT DOCUMENTS

| | | | |
|---|---|---|---|
| 2007/0078444 A1 | 4/2007 | Larsson | |
| 2007/0106177 A1 | 5/2007 | Hama | |
| 2007/0145137 A1 | 6/2007 | Mrowiec | |
| 2007/0225668 A1 | 9/2007 | Otto | |
| 2007/0252714 A1 | 11/2007 | Rondoni et al. | |
| 2008/0027409 A1 | 1/2008 | Rudko et al. | |
| 2008/0217391 A1 | 9/2008 | Roof et al. | |
| 2008/0312550 A1 | 12/2008 | Nishtala et al. | |
| 2008/0312556 A1 | 12/2008 | Dijkman | |
| 2009/0056020 A1 | 3/2009 | Caminade et al. | |
| 2009/0099629 A1 | 4/2009 | Carson et al. | |
| 2009/0157430 A1 | 6/2009 | Rule et al. | |
| 2009/0287170 A1 | 11/2009 | Otto | |
| 2009/0315684 A1 | 12/2009 | Sacco et al. | |
| 2010/0064426 A1 | 3/2010 | Chikara Imamura | |
| 2010/0094204 A1 | 4/2010 | Nishtala | |
| 2010/0130949 A1 | 5/2010 | Garcia | |
| 2010/0137743 A1 | 6/2010 | Nishtala et al. | |
| 2010/0262047 A1 | 10/2010 | Genis | |
| 2011/0113540 A1 | 5/2011 | Plate et al. | |
| 2011/0120219 A1 | 5/2011 | Barlesi et al. | |
| 2011/0178425 A1 | 7/2011 | Nishtala et al. | |
| 2011/0224636 A1 | 9/2011 | Keisic | |
| 2011/0230824 A1 | 9/2011 | Salinas et al. | |
| 2011/0238042 A1 | 9/2011 | Davis et al. | |
| 2011/0251572 A1 | 10/2011 | Nishtala et al. | |
| 2011/0263952 A1 | 10/2011 | Bergman et al. | |
| 2012/0029408 A1 | 2/2012 | Beaudin | |
| 2012/0035496 A1* | 2/2012 | Denison | A61B 5/7203 |
| | | | 600/547 |
| 2012/0059286 A1 | 3/2012 | Hastings et al. | |
| 2012/0078137 A1 | 3/2012 | Mendels et al. | |
| 2012/0078235 A1 | 3/2012 | Martin et al. | |
| 2012/0095304 A1 | 4/2012 | Biondi | |
| 2012/0109008 A1 | 5/2012 | Charlez et al. | |
| 2012/0118650 A1 | 5/2012 | Gill | |
| 2012/0123233 A1 | 5/2012 | Cohen | |
| 2012/0127103 A1 | 5/2012 | Qualey et al. | |
| 2012/0226196 A1 | 9/2012 | DiMino et al. | |
| 2012/0234434 A1 | 9/2012 | Woodruff et al. | |
| 2012/0302917 A1 | 11/2012 | Fitzgerald et al. | |
| 2012/0323144 A1 | 12/2012 | Coston et al. | |
| 2012/0323502 A1 | 12/2012 | Tanoura et al. | |
| 2013/0066166 A1 | 3/2013 | Burnett et al. | |
| 2013/0109927 A1 | 5/2013 | Menzel | |
| 2013/0109928 A1 | 5/2013 | Menzel | |
| 2013/0131610 A1 | 5/2013 | Dewaele et al. | |
| 2013/0218106 A1 | 8/2013 | Coston et al. | |
| 2013/0245498 A1 | 9/2013 | Delaney et al. | |
| 2013/0267871 A1 | 10/2013 | Delaney et al. | |
| 2014/0039348 A1 | 2/2014 | Bullington et al. | |
| 2014/0155781 A1 | 6/2014 | Bullington et al. | |
| 2014/0155782 A1 | 6/2014 | Bullington et al. | |
| 2014/0159921 A1 | 6/2014 | Qualey et al. | |
| 2014/0187666 A1 | 7/2014 | Aizenberg et al. | |
| 2014/0207085 A1 | 7/2014 | Brandt et al. | |
| 2014/0243635 A1 | 8/2014 | Arefieg | |
| 2014/0335490 A1 | 11/2014 | Baarman et al. | |
| 2015/0120321 A1 | 4/2015 | David et al. | |
| 2015/0233749 A1 | 8/2015 | Wang et al. | |
| 2015/0342576 A1 | 12/2015 | Hall et al. | |
| 2015/0343173 A1 | 12/2015 | Tobescu et al. | |
| 2015/0359522 A1 | 12/2015 | Recht et al. | |
| 2015/0362351 A1 | 12/2015 | Joshi et al. | |
| 2016/0051176 A1 | 2/2016 | Ramos et al. | |
| 2016/0051177 A1 | 2/2016 | Chen | |
| 2016/0183819 A1 | 6/2016 | Burnett et al. | |
| 2016/0374874 A1 | 12/2016 | Trepanier et al. | |
| 2017/0035342 A1 | 2/2017 | Elia et al. | |
| 2017/0043089 A1 | 2/2017 | Handler | |
| 2017/0100068 A1 | 4/2017 | Kostov | |
| 2017/0113000 A1 | 4/2017 | Tobescu et al. | |
| 2017/0136209 A1 | 5/2017 | Burnett et al. | |
| 2017/0140103 A1 | 5/2017 | Angelides | |
| 2017/0196478 A1 | 7/2017 | Hunter | |
| 2017/0202698 A1 | 7/2017 | Zani et al. | |
| 2017/0241978 A1 | 8/2017 | Duval | |
| 2017/0249445 A1 | 8/2017 | Devries et al. | |
| 2017/0290540 A1 | 10/2017 | Franco | |
| 2017/0291012 A1 | 10/2017 | Iglesias | |
| 2017/0307423 A1 | 10/2017 | Pahwa et al. | |
| 2017/0322197 A1 | 11/2017 | Hall et al. | |
| 2018/0015251 A1 | 1/2018 | Lampotang et al. | |
| 2018/0110455 A1 | 4/2018 | Chang et al. | |
| 2018/0110456 A1 | 4/2018 | Cooper et al. | |
| 2018/0160961 A1* | 6/2018 | Gopinathan | A61B 5/00 |
| 2018/0214122 A1* | 8/2018 | Ansell | G16H 50/20 |
| 2018/0214297 A1 | 8/2018 | Hughett et al. | |
| 2018/0245967 A1 | 8/2018 | Parker et al. | |
| 2018/0280236 A1 | 10/2018 | Udin et al. | |
| 2018/0317891 A1 | 11/2018 | Kim | |
| 2018/0344234 A1 | 12/2018 | McKinney et al. | |
| 2019/0006047 A1 | 1/2019 | Gorek et al. | |
| 2019/0017535 A1 | 1/2019 | Ormsbee et al. | |
| 2019/0046102 A1 | 2/2019 | Kushnir et al. | |
| 2019/0069829 A1 | 3/2019 | Bulut | |
| 2019/0069830 A1 | 3/2019 | Holt et al. | |
| 2019/0126006 A1 | 5/2019 | Rehm et al. | |
| 2019/0150821 A1* | 5/2019 | Waters | A61B 5/1112 |
| 2019/0167144 A1* | 6/2019 | Jung | A61B 5/7278 |
| 2019/0201596 A1 | 7/2019 | Luxon et al. | |
| 2019/0223844 A1 | 7/2019 | Aboagye et al. | |
| 2019/0231244 A1 | 8/2019 | Swan et al. | |
| 2019/0247236 A1 | 8/2019 | Sides et al. | |
| 2019/0254582 A1 | 8/2019 | Wei et al. | |
| 2019/0298317 A1 | 10/2019 | Colgan et al. | |
| 2019/0321588 A1 | 10/2019 | Burnett et al. | |
| 2019/0328945 A1 | 10/2019 | Analytis et al. | |
| 2019/0343445 A1 | 11/2019 | Burnett et al. | |
| 2019/0358387 A1* | 11/2019 | Elbadry | A61B 5/0059 |
| 2019/0365308 A1 | 12/2019 | Laing et al. | |
| 2019/0381223 A1 | 12/2019 | Culbert et al. | |
| 2020/0022637 A1 | 1/2020 | Kurzrock et al. | |
| 2020/0064172 A1 | 2/2020 | Tabaczewski et al. | |
| 2020/0085378 A1 | 3/2020 | Burnett et al. | |
| 2020/0121300 A1 | 4/2020 | Moore | |
| 2020/0187863 A1 | 6/2020 | Tu et al. | |
| 2020/0268302 A1* | 8/2020 | Oh | A61B 5/227 |
| 2020/0268303 A1 | 8/2020 | Oliva | |
| 2020/0289749 A1 | 9/2020 | Odashima et al. | |
| 2020/0405524 A1 | 12/2020 | Gill | |
| 2021/0054610 A1 | 2/2021 | Hall et al. | |
| 2021/0077007 A1 | 3/2021 | Jouret et al. | |
| 2021/0100533 A1 | 4/2021 | Seres et al. | |
| 2021/0113130 A1 | 4/2021 | Tran | |
| 2021/0299353 A1 | 9/2021 | Mannu et al. | |
| 2021/0361211 A1 | 11/2021 | Teramoto et al. | |
| 2022/0018692 A1 | 1/2022 | Tourchak et al. | |
| 2022/0026001 A1 | 1/2022 | Cheng et al. | |
| 2022/0026261 A1 | 1/2022 | Funnell et al. | |
| 2022/0079487 A1 | 3/2022 | Horiguchi et al. | |
| 2022/0192564 A1 | 6/2022 | Kriscovich et al. | |
| 2022/0192565 A1 | 6/2022 | Cheng et al. | |
| 2022/0192566 A1 | 6/2022 | Cheng et al. | |
| 2022/0193375 A1 | 6/2022 | Rehm et al. | |
| 2022/0233120 A1 | 7/2022 | Beuret et al. | |
| 2022/0296140 A1 | 9/2022 | Nguyen et al. | |
| 2022/0330867 A1 | 10/2022 | Conley et al. | |
| 2022/0386917 A1 | 12/2022 | Mann et al. | |
| 2023/0019703 A1 | 1/2023 | Behzad et al. | |
| 2023/0022547 A1 | 1/2023 | Cho et al. | |
| 2023/0025333 A1 | 1/2023 | Patel et al. | |
| 2023/0028966 A1 | 1/2023 | Franano | |
| 2023/0035669 A1 | 2/2023 | Raja et al. | |
| 2023/0040915 A1 | 2/2023 | Compton et al. | |
| 2023/0058553 A1 | 2/2023 | Fallows et al. | |
| 2023/0060232 A1 | 3/2023 | Patel et al. | |
| 2023/0084476 A1 | 3/2023 | Robichaud et al. | |
| 2023/0089041 A1 | 3/2023 | Handler | |
| 2024/0042120 A1 | 2/2024 | Cheng et al. | |
| 2024/0108268 A1 | 4/2024 | Woodard et al. | |
| 2024/0252783 A1 | 8/2024 | Waitkus et al. | |
| 2024/0347162 A1 | 10/2024 | Meese et al. | |
| 2024/0360938 A1 | 10/2024 | Cheng et al. | |

(56) References Cited

U.S. PATENT DOCUMENTS

| 2024/0424186 | A1 | 12/2024 | Justice et al. |
| 2025/0090066 | A1 | 3/2025 | Tourchak |
| 2025/0120636 | A1 | 4/2025 | Compton et al. |
| 2025/0205456 | A1 | 6/2025 | Rehm et al. |
| 2025/0339073 | A1 | 11/2025 | Cheng et al. |

FOREIGN PATENT DOCUMENTS

| CN | 200951235 | Y | 9/2007 |
| CN | 201492414 | U | 6/2010 |
| CN | 102647939 | A | 8/2012 |
| CN | 103054559 | B | 5/2015 |
| CN | 104921738 | A | 9/2015 |
| CN | 107952140 | A | 4/2018 |
| CN | 109498013 | A | 3/2019 |
| CN | 110859636 | A | 3/2020 |
| CN | 112426156 | A | 3/2021 |
| EP | 0342028 | A2 | 11/1989 |
| ES | 2760470 | T3 | 5/2020 |
| GB | 2437549 | A | 10/2007 |
| GB | 2576743 | A | 3/2020 |
| JP | S4975171 | A | 7/1974 |
| JP | S54147066 | A | 11/1979 |
| JP | S58190719 | A | 11/1983 |
| JP | S60219517 | A | 11/1985 |
| JP | H02057240 | B2 | 12/1990 |
| JP | H08271301 | A | 10/1996 |
| JP | H10104041 | A | 4/1998 |
| JP | 2007303982 | A | 11/2007 |
| JP | 2008524618 | A | 7/2008 |
| JP | 2009068959 | A | 4/2009 |
| JP | 2010121950 | A | 6/2010 |
| JP | 2010530978 | A | 9/2010 |
| JP | 2012105947 | A | 6/2012 |
| JP | 2012225790 | A | 11/2012 |
| JP | 2018108356 | A | 7/2018 |
| KR | 20070115495 | A | 12/2007 |
| NL | 2013740 | A | 8/2016 |
| RU | 2615727 | C2 | 4/2017 |
| WO | 1981003427 | A1 | 12/1981 |
| WO | 2004045410 | A1 | 6/2004 |
| WO | 2013013782 | A2 | 1/2013 |
| WO | 20130178742 | A1 | 12/2013 |
| WO | 2014043650 | A2 | 3/2014 |
| WO | 2014105755 | A1 | 7/2014 |
| WO | 2014108690 | A1 | 7/2014 |
| WO | 2014135856 | A1 | 9/2014 |
| WO | 2014145971 | A2 | 9/2014 |
| WO | 2014151068 | A2 | 9/2014 |
| WO | 201511402 | A1 | 1/2015 |
| WO | 2015105916 | A1 | 7/2015 |
| WO | 2015127390 | A1 | 8/2015 |
| WO | 2015191125 | A1 | 12/2015 |
| WO | 2016177901 | A1 | 11/2016 |
| WO | 2017023794 | A1 | 2/2017 |
| WO | 2018156624 | A1 | 8/2018 |
| WO | 2019066357 | A1 | 4/2019 |
| WO | 2019106675 | A1 | 6/2019 |
| WO | 2019226697 | A1 | 11/2019 |
| WO | 2020033752 | A1 | 2/2020 |
| WO | 2020154370 | A1 | 7/2020 |
| WO | 2020251893 | A1 | 12/2020 |
| WO | 2022108589 | A1 | 5/2022 |
| WO | 2022182794 | A1 | 9/2022 |
| WO | 2023022895 | A1 | 2/2023 |
| WO | 2023027871 | A1 | 3/2023 |
| WO | 2023076067 | A1 | 5/2023 |

OTHER PUBLICATIONS

PCT/US2019/033389 filed Nov. 26, 2020 Extended European Search Report dated Jun. 4, 2021.
U.S. Appl. No. 17/054,493, filed Nov. 10, 2020 Final Office Action dated Oct. 4, 2023.
U.S. Appl. No. 17/054,493, filed Nov. 10, 2020 Notice of Allowance dated Jan. 4, 2024.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/373,546, filed Jul. 12, 2021 Non-Final Office Action dated Nov. 1, 2023.
U.S. Appl. No. 17/556,907, filed Dec. 20, 2021 Notice of Allowance dated Dec. 6, 2023.
EP 20962628.2 filed May 31, 2023 Extended European Search Report dated Apr. 20, 2024.
PCT/US2022/039191 filed Aug. 2, 2022 International Search Report and Written Opinion dated Dec. 5, 2022.
PCT/US2022/039746 filed Aug. 8, 2022 International Search Report and Written Opinion dated Nov. 18, 2022.
U.S. Appl. No. 17/306,821, filed May 3, 2021 Notice of Allowance dated Apr. 23, 2024.
U.S. Appl. No. 17/373,546, filed Jul. 12, 2021 Notice of Allowance dated Mar. 7, 2024.
U.S. Appl. No. 17/373,546, filed Jul. 12, 2021 Notice of Allowance dated May 29, 2024.
U.S. Appl. No. 17/556,931, filed Dec. 20, 2021 Non-Final Office Action dated Mar. 27, 2024.
U.S. Appl. No. 17/556,931, filed Dec. 20, 2021 Restriction Requirement dated Feb. 22, 2024.
"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).
PCT/US2022/046920 filed Oct. 17, 2022 International Search Report and Written Opinion dated Feb. 20, 2023.
U.S. Appl. No. 17/552,250, filed Dec. 15, 2021 Non-Final Office Action dated Sep. 19, 2024.
U.S. Appl. No. 17/556,931, filed Dec. 20, 2021 Advisory Action dated Dec. 6, 2024.
U.S. Appl. No. 17/556,931, filed Dec. 20, 2021 Final Office Action dated Oct. 1, 2024.
U.S. Appl. No. 17/560,079, filed Dec. 22, 2021 Notice of Allowance dated Oct. 29, 2024.
Bard Medical, Criticore Disposables—Non I.C., 3 pages, www.bardmedical.com/products/patienl-moniloring-,ystems/criticore®-system/criticore®-disposables-non-ic/ Jan. 30, 2015.
Bard Medical, Criticore Infection Control Disposables, 3 pages, www.bardmedical.com/patienl-moniloring-,ystems/criticore®-system/criticore®-infection-control-disposables/ Jan. 30, 2015.
Bard Medical, Criticore Monitor, 11 pages, www.bardmedical.com/products/patient-monitoring-systems/criticore®--monitor/ Jan. 30, 2015.
Bard Medical, Urine Meiers, 3 pages, www.bardmedical.com/products/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
DFree Personal—Consumer Product Brochure, 2019.
DFree Pro Brochure 2019.
Leonhauser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary vol. Monitoring System Based on Bio-Impedance."—Engineering; vol. 5; pp. 321-325; 2013.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US20/61367 filed Nov. 19, 2020 International Search Report and Written Opinion dated Feb. 22, 2021.
PCT/US2016/044835 filed Jul. 20, 2016 International Search Report and Written Opinion dated Dec. 16, 2016.
PCT/US2019/045787 filed Aug. 8, 2019 International Preliminary Report on Patentability dated Feb. 16, 2021.

(56) References Cited

OTHER PUBLICATIONS

PCT/US2019/045787 filed Aug. 8, 2019 International Search Report and Written Opinion dated Oct. 2, 2019.
PCT/US2022/017574 filed Feb. 23, 2022 Internation Search Report and Written Opinion dated Jun. 8, 2022.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper, Mar. 2020.
Schlebusch, T. et al., "Bladder vol. estimation from electrical impedance tomography" Physiological Measurement, Institute of Physics, Bristol, GB. vol. 35 No. 9 Aug. 20, 2014. (Aug. 20, 2014).
SECA product catalog, https://us.secashop.com/products/seca-mbca/seca-mbca-514/5141321139, last accessed Sep. 11, 2020.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 15/748,107, filed Jan. 26, 2018 Notice of Allowance dated Dec. 12, 2022.
U.S. Appl. No. 17/054,493, filed Nov. 10, 2020 Final Office Action dated May 31, 2022.
U.S. Appl. No. 17/054,493, filed Nov. 10, 2020 Non-Final Office Action dated Jan. 27, 2023.
U.S. Appl. No. 17/054,493, filed Nov. 10, 2020 Non-Final Office Action dated Nov. 24, 2021.
U.S. Appl. No. 17/262,080, filed Jan. 21, 2021 Final Office Action dated Sep. 11, 2023.
U.S. Appl. No. 17/262,080, filed Jan. 21, 2021 Non-Final Office Action dated Apr. 6, 2023.
U.S. Appl. No. 17/306,821, filed May 3, 2021 Final Office Action dated Jul. 19, 2023.
U.S. Appl. No. 17/306,821, filed May 3, 2021 Non-Final Office Action dated Jan. 10, 2023.
U.S. Appl. No. 17/373,535, filed Jul. 12, 2021 Non-Final Office Action dated November 9. 2022.
U.S. Appl. No. 17/373,535, filed Jul. 12, 2021 Notice of Allowance dated Feb. 23. 2023.
U.S. Appl. No. 17/556,907, filed Dec. 20, 2021 Non-Final Office Action dated Aug. 17, 2023.
U.S. Appl. No. 17/556,907, filed Dec. 20, 2021 Restriction Requirement dated May 12, 2023.
"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/552,250, filed Dec. 15, 2021 Final Office Action dated Feb. 11, 2025.
U.S. Appl. No. 17/556,931, filed Dec. 20, 2021 Notice of Allowance dated Mar. 18, 2025.
U.S. Appl. No. 17/587,938, filed Jan. 28, 2022 Restriction Requirement dated Jan. 22, 2025.
U.S. Appl. No. 17/833,682, filed Jun. 6, 2022 Non-Final Office Action dated Jan. 15, 2025.
U.S. Appl. No. 17/870,698, filed Jul. 21, 2022 Restriction Requirement dated Feb. 12, 2025.
U.S. Appl. No. 17/879,658, filed Aug. 2, 2022 Non-Final Office Action dated Dec. 30, 2024.
U.S. Appl. No. 17/893,435, filed Aug. 23, 2022 Non-Final Office Action dated Jan. 17, 2025.
U.S. Appl. No. 17/863,223, filed Jul. 12, 2022 Advisory Action dated Dec. 1, 2025.
U.S. Appl. No. 17/863,223, filed Jul. 12, 2022 Final Office Action dated Sep. 24, 2025.
U.S. Appl. No. 17/863,923, filed Jul. 13, 2022 Non-Final Office Action dated Oct. 22, 2025.
U.S. Appl. No. 17/870,698, filed Jul. 21, 2022 Non-Final Office Action dated Nov. 21, 2025.
U.S. Appl. No. 17/873,834, filed Jul. 26, 2022 Final Office Action dated Nov. 28, 2025.
U.S. Appl. No. 17/879,658, filed Aug. 2, 2022 Non-Final Office Action dated Nov. 18, 2025.
U.S. Appl. No. 18/036,335, filed May 10, 2023 Notice of Allowance dated Oct. 21, 2025.
U.S. Appl. No. 17/552,250, filed Dec. 15, 2021 Advisory Action dated May 8, 2025.
U.S. Appl. No. 17/552,250, filed Dec. 15, 2021 Notice of Allowance dated May 20, 2025.
U.S. Appl. No. 17/587,938, filed Jan. 28, 2022 Non-Final Office Action dated May 12, 2025.
U.S. Appl. No. 17/682,785, filed Feb. 28, 2022 Non-Final Office Action dated Jul. 16, 2025.
U.S. Appl. No. 17/682,785, filed Feb. 28, 2022 Restriction Requirement dated Apr. 2, 2025.
U.S. Appl. No. 17/833,682, filed Jun. 6, 2022 Final Office Action dated May 12, 2025.
U.S. Appl. No. 17/833,682, filed Jun. 6, 2022 Non-Final Office Action dated Sep. 15, 2025.
U.S. Appl. No. 17/863,223, filed Jul. 12, 2022 Non-Final Office Action dated Apr. 2, 2025.
U.S. Appl. No. 17/863,923, filed Jul. 13, 2022 Restriction Requirement dated May 21, 2025.
U.S. Appl. No. 17/870,698, filed Jul. 21, 2022 Final Office Action dated Jul. 29, 2025.
U.S. Appl. No. 17/870,698, filed Jul. 21, 2022 Non-Final Office Action dated Apr. 9, 2025.
U.S. Appl. No. 17/873,834, filed Jul. 26, 2022 Non-Final Office Action dated May 19, 2025.
U.S. Appl. No. 17/879,658, filed Aug. 2, 2022 Final Office Action dated May 14, 2025.
U.S. Appl. No. 17/883,507, filed Aug. 8, 2022 Non-Final Office Action dated Aug. 27, 2025.
U.S. Appl. No. 17/883,507, filed Aug. 8, 2022 Restriction Requirement dated May 19, 2025.
U.S. Appl. No. 17/893,435, filed Aug. 23, 2022 Notice of Allowance dated Jul. 11, 2025.
U.S. Appl. No. 17/941,941, filed Sep. 9, 2022 Non-Final Office Action dated Aug. 22, 2025.
U.S. Appl. No. 17/941,941, filed Sep. 9, 2022 Restriction Requirement dated May 28, 2025.
U.S. Appl. No. 18/036,335, filed May 10, 2023 Non-Final Office Action dated Jun. 18, 2025.
U.S. Appl. No. 18/682,075, filed Feb. 7, 2024 Non-Final Office Action dated Jun. 18, 2025.
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).

* cited by examiner

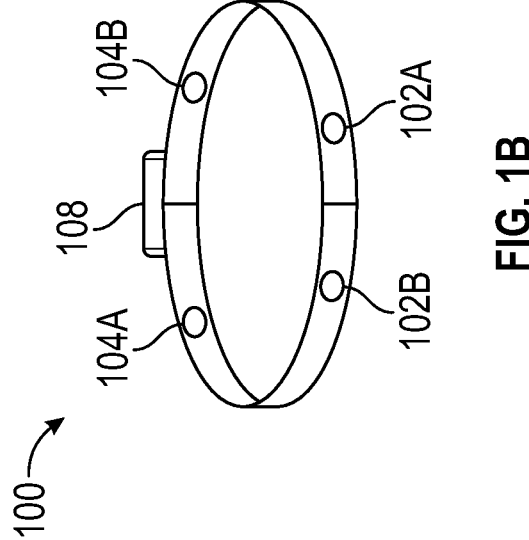
FIG. 1B
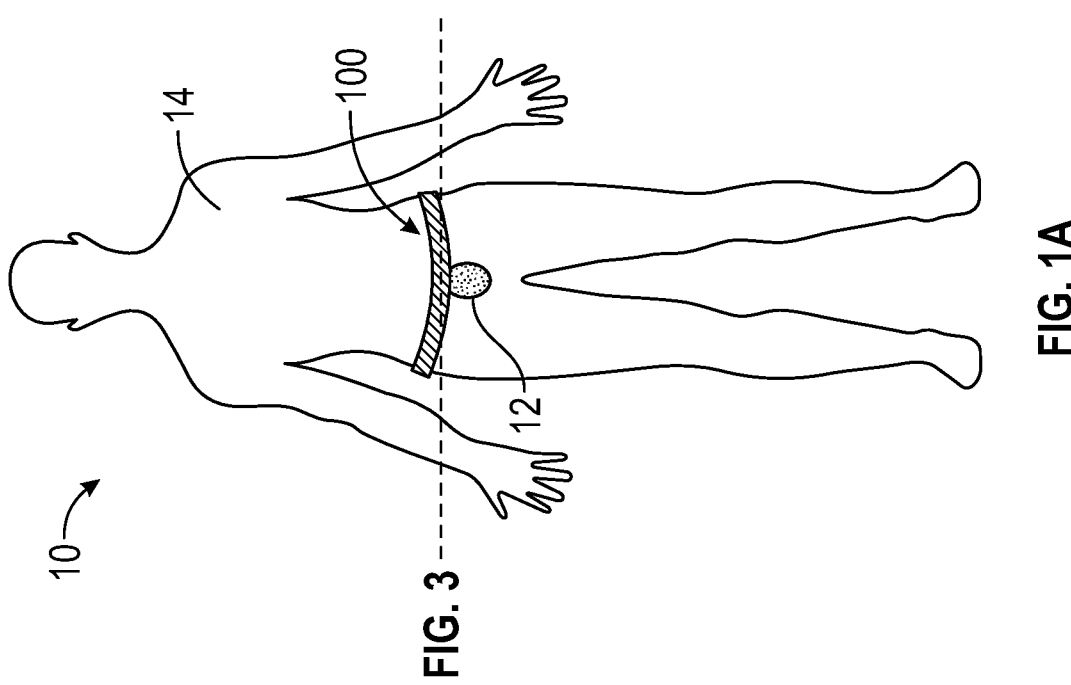
FIG. 1A
FIG. 3

100

126

104

108

108

102

102    102    102

SKIN SURFACE SIDE

OUTER SIDE

SELF-LEARNING AND NON-INVASIVE BLADDER MONITORING SYSTEMS AND METHODS

PRIORITY

This application is a U.S. national stage application of International Application No. PCT/US2022/017574, filed Feb. 23, 2022, which claims the benefit of priority to U.S. Provisional Application No. 63/152,689, filed Feb. 23, 2021, to U.S. Provisional Application No. 63/157,530, filed Mar. 5, 2021, and to U.S. Provisional Application No. 63/152, 715, filed Feb. 23, 2021, each of which is incorporated by reference in its entirety into this application.

SUMMARY

Briefly summarized, embodiments disclosed herein are directed to a self-learning and non-invasive bladder volume ("BV") monitoring, voiding volume measurement, and total body water monitoring systems and associated methods thereof. Embodiments can use bio-impedance spectroscopy ("BIS") and can be free-standing or worn by the patient.

Heart failure ("HF") is one of the most common causes of hospitalizations, causing patients to present with edema and other symptoms of fluid overload due to the weakened heart. The most common treatment for these patients is diuretics to remove excess fluid via urination and relieve the fluid burden on the heart. Patient urine output ("UO") and total body water ("TBW") are key metrics for evaluating patient response to diuretic treatment. However, gathering accurate UO and TBW data can be challenging.

HF and similar patients admitted to the ICU or similar critical care environments can have indwelling urinary catheters (Foley catheters) inserted, the output from these can be used to measure UO. Similarly, external catheter systems may be used, the output from these can also be used to measure UO. Some patients may be managed via intermittent catheterization. In these patients, a provider will periodically measure the patient's bladder volume with a portable ultrasound device or scanner. If the patient's bladder is sufficiently full, the provider will perform an intermittent catheterization procedure to drain the bladder. This process, while reducing the infection risk associated with an indwelling urinary catheter, does require periodic assessment by the provider with a portable ultrasound bladder scanner which is both time-consuming for the provider and potentially interruptive to the patient. Alternatively, HF and similar patients can be semi-ambulatory and admitted to the general ward where accurate UO collection, measurement, and recording presents a large clinical challenge.

Current techniques for measuring UO of semi-ambulatory patients use a variety of devices, such as urinary hats, bedside commodes, graduated urinals, and bedpans. However, these solutions have several limitations. Urinary hats and other collection devices present infection control issues and are frequently knocked over by patients or nurses, which may lose several hours of UO data. Inaccurate voiding directly into the collection device can also result in the loss of some UO data and inaccurate results. In addition, hospital staff must rely on patient ability and compliance to help collect, measure, and sometimes even record their UO data. Further, the time of the void is often not accurately captured thus limiting an assessment of kidney function by providers who wish to know the volume of urine produced during a specific interval of time. As such, manual measurement and recording of UO data by either patient or trained clinician leaves opportunity for errors and also opportunities for greater risk of cross-contamination. Further, voided fluid is not always an accurate representation of UO for a patient since a residual amount of fluid remains in the bladder after the voiding event (termed post-voiding fluid volume). The residual, post-voiding fluid volume can vary greatly depending on the patient. As such, comparing the pre-voiding bladder volume with the post-voiding fluid volume and voided fluid volume can provide improved UO data for a patient.

Gathering accurate TBW can also be challenging. Most TBW measurement systems require additional information about the patient, e.g. age, weight, height, gender, ethnicity, demographics, etc. and then apply regression based algorithms based on what is "normal" for these patient parameters. However, such systems fail to account for atypical patients, such as HF patients or those in similar critical care situations. Moreover, the need for high levels of accuracy in such atypical patients is more significant, since small degrees of change can have dramatic consequences compared to those seen in normal, healthy individuals.

Embodiments described herein are directed to self-learning, non-invasive UO and TBW measuring devices, and associated methods thereof, which can be integrated into the health care professional's work flow. These devices can use bio-impedance spectroscopy ("BIS") to accurately determine a patient's TBW/UO values without relying exclusively on population specific assumptions or regression based algorithms. Embodiments include devices that can be free-standing, or can be wearable, and can be used for bedridden, semi-ambulatory, or ambulatory patients.

Disclosed herein is a system for measuring a volume of fluid within a bladder of a patient including, a bladder volume monitoring system including an impedance sensor contacting a skin surface of the patient, the bladder volume monitoring system configured to measure an electrical impedance of a bladder portion of the patient and determine a bladder volume value for the patient using a model, wherein the bladder volume value is an estimated volume of fluid within the bladder, a training system configured to receive a urine output value for a volume of fluid voided from the bladder, and a logic configured to determine a difference between the pre- and post-void bladder volume values and the urine output value and iteratively modify the model to reduce the difference between the pre- and post-void bladder volume value and the urine output value to improve the accuracy of the model.

In some embodiments, the bladder volume monitoring system uses one of bio-impedance analysis, bio-impedance spectroscopy, bio-impedance plethysmography, or bio-impedance tomography to determine the bladder volume value.

In some embodiments, the bladder volume monitoring system is configured to measure a first electrical impedance value before a voiding event and a second electrical impedance value after the voiding event to determine the bladder volume value.

In some embodiments, the impedance sensor includes a first sensor array having a first electrode configured to provide an excitation signal and a second electrode configured to measure an electric impedance of the excitation signal through the bladder portion of the patient.

In some embodiments, the bladder volume monitoring system further includes a second sensor array including a third electrode configured to provide a second excitation signal and a fourth electrode configured to measure a second electric impedance of the second excitation signal through a second portion of the patient to determine a total body water value for the patient.

In some embodiments, the logic retrieves the total body water value and further modifies the model to reduce the difference between the bladder volume value and the urine output value to improve the accuracy of the model.

In some embodiments, the automatic urine output training system includes a flow sensor coupled with one of a catheter, a drainage tube, or a collection container and configured to determine the urine output value.

In some embodiments, the training system includes an automatic urine output training system including a valve configured to control a flow of fluid voided from the bladder and to train the bladder of the patient to a natural bladder cycle.

In some embodiments, the training system includes an interface to a network or electronic health record system configured to receive a voided fluid volume input.

In some embodiments, the training system includes a user interface configured to receive a voided fluid volume input.

In some embodiments, the impedance sensor is disposed on a belt secured about the patient's waist and configured to align the impedance sensor with the bladder portion of the patient.

In some embodiments, the bladder volume monitoring system further includes an accelerometer or a gyroscope configured to detect a movement of the patient, the logic configured to receive a signal from the one of the accelerometer or the gyroscope and modify the model to improve the accuracy of the bladder volume value for the patient.

In some embodiments, the bladder volume monitoring system further includes an electromyography sensor in contact with a skin surface of the patient and configured to detect one of a contraction of a detrusor muscle, or a relaxation of a urinary sphincter of the patient to determine an occurrence of a bladder voiding event.

In some embodiments, the system is communicatively coupled with one of a network, a remote database, an intranet, an internet, a cloud-based network, or an electronic health record system.

In some embodiments, the impedance sensor is in wireless communication with the bladder volume monitoring system, and wherein one of the bladder volume monitoring system, the training system, or the logic are disposed within a stand-alone unit.

In some embodiments, the stand-alone unit includes one of a base station, a portable computing device, a monitor, a handheld device, a wearable device, a smart watch, a laptop, or a tablet device.

In some embodiments, the training system further includes one or both of an ultrasound training system and a pressure based training system.

Also disclosed is a bladder volume measuring system including, a first sensor array including an electrode in contact with a skin surface of a patient, the first sensor array configured to determine an electrical impedance value of a bladder of the patient, an ultrasound system including a transducer in contact with the skin surface of the patient, the ultrasound system configured to determine a volume of fluid within the bladder of the patient, and a bladder volume monitoring system including logic configured to determine a volume of fluid within the bladder from the electrical impedance value using a bladder volume model, and configured to iteratively verify the bladder volume model with the volume of fluid within the bladder as determined by the ultrasound system.

In some embodiments, one of the first sensor array or the transducer are disposed on a belt configured to encircle a waist portion of the patient and secure the one of the first sensor array or the transducer to the skin surface of the patient.

In some embodiments, the urine volume monitoring system uses one of bio-impedance analysis, bio-impedance spectroscopy, bio-impedance plethysmography, or bio-impedance tomography to determine the volume of fluid within the bladder from the electrical impedance value.

In some embodiments, the first sensor array includes a first electrode configured to provide an excitation signal and a second electrode configured to measure an electric impedance of the excitation signal through the bladder of the patient.

In some embodiments, the urine volume monitoring system further includes a second sensor array including a third electrode configured to provide a second excitation signal and a fourth electrode configured to measure a second electric impedance of the second excitation signal through a second portion of the patient to determine a total body water value for the patient.

In some embodiments, the urine volume monitoring system logic retrieves the total body water value and modifies the bladder volume model to improve the accuracy of the bladder volume model for the patient.

In some embodiments, the bladder volume measuring system further includes an accelerometer or a gyroscope configured to detect a movement of the patient, the urine volume monitoring system logic configured to receive a signal from one of the accelerometer or the gyroscope and modify the bladder volume model to improve the accuracy of the bladder volume model for the patient.

In some embodiments, the bladder volume measuring system further includes an electromyography sensor in contact with a skin surface of the patient and configured to detect one of a contraction of a detrusor muscle or a relaxation of a urinary sphincter of the patient to determine an occurrence of a bladder voiding event.

In some embodiments, the urine volume monitoring system logic is communicatively coupled with one of a network, a remote database, an intranet, an internet, a cloud-based network, or an electronic health record system.

In some embodiments, the first sensor array is in wireless communication with the urine volume monitoring system, and wherein one of the urine volume monitoring system or the ultrasound system are disposed within a stand-alone unit.

In some embodiments, the stand-alone unit includes one of a base station, a portable computing device, a monitor, a handheld device, a wearable device, a smart watch, a laptop, or a tablet device.

In some embodiments, the bladder volume system further includes a user interface configured to receive a voided fluid volume input.

In some embodiments, the ultrasound transducer or system may be removed from the system after sufficient training of the electrical impedance component of the bladder volume system.

Also disclosed is a method of measuring a volume of fluid within a bladder of a patient including, measuring a first electrical impedance value for the bladder of the patient, determining a volume of fluid within the bladder from the electrical impedance value using a bladder volume model, measuring a volume of fluid voided from the bladder, and modifying the bladder volume model to minimize the difference between the volume of fluid within the bladder as determined by the electrical impedance value and the volume of fluid voided from the bladder.

In some embodiments, the method further includes measuring the first electrical impedance value before the volume of fluid is voided from the bladder and measuring a second electrical impedance value after the volume of fluid is voided from the bladder to determine the volume of fluid originally within the bladder.

In some embodiments, the method further includes using one of bio-impedance analysis, bio-impedance spectroscopy, bio-impedance plethysmography, or bio-impedance tomography to determine the volume of fluid within the bladder from the electrical impedance value.

In some embodiments, the method further includes measuring an electrical impedance value for a body portion of the patient, determining a total body water value for the patient and modifying the bladder volume model to improve the accuracy of the bladder volume model in determining the volume of fluid within the bladder.

In some embodiments, measuring an electrical impedance value for the bladder of the patient includes a first sensor array including a first electrode configured to provide an excitation signal and a second electrode configured to measure an electric impedance of the excitation signal through the bladder of the patient.

In some embodiments, the method further includes detecting a movement of the patient using one of an accelerometer or a gyroscope and modifying the bladder volume model to improve the accuracy of the bladder volume model in determining a volume of fluid within the bladder from the electrical impedance value.

In some embodiments, the method further includes detecting one of a contraction of a detrusor muscle or a relaxation of a urinary sphincter of the patient to determine an occurrence of a bladder voiding event using an electromyography sensor in contact with a skin surface of the patient.

In some embodiments, the method further includes communicating a value for the volume of fluid within the bladder, or the volume of fluid voided from the bladder with one of a network, a remote database, an intranet, an internet, a cloud-based network, or an electronic health record system.

In some embodiments, the method further includes controlling a flow of fluid voided from the bladder to improve the bladder volume model and to train the bladder of the patient to a natural bladder cycle.

In some embodiments, the method further includes a training system configured to determine a first volume of fluid within the bladder before the volume of fluid is voided from the bladder and a second volume of fluid within the bladder after the volume of fluid is voided from the bladder.

In some embodiments, the training system includes one of an ultrasound training system, an automatic urine output training system, or a bladder pressure training system, a network or electronic health record-connected training system, or a user input training system.

Also disclosed is a device for measuring a volume of fluid disposed within the bladder of the patient including, an article of clothing secured about at least a waist portion of the patient, a sensor disposed on an inner surface of the article of clothing, and a computing device communicatively coupled with the sensor and including logic configured to determine a volume of fluid disposed within a bladder of the patient.

In some embodiments, the article of clothing includes a T-shirt, briefs, disposable undergarment, or a belt. The sensor includes one of an electrical impedance modality, ultrasound modality, or optical laser modality. In some embodiments, the device further includes a first sensor array including a first electrode and a second electrode positioned proximate the bladder of the patient and configured to determine a volume of fluid disposed within the bladder using a bio-impedance spectroscopy. In some embodiments, the device further includes a second sensor array configured to determine a total body water metric. In some embodiments, the computing device is communicatively coupled with one of a network or an electronic health record system.

Also disclosed is a bladder volume measuring device including, a sensor array configured to detect an electrical impedance value for a bladder of a patient, and a BV logic configured to determine a volume of fluid disposed within the bladder from the electrical impedance value using bio-impedance spectroscopy.

In some embodiments, the bladder volume measuring device further includes a second sensor array configured to detect a second electrical impedance value for a body portion of a patient, the BV logic configured to determine a total body water value from the second electrical impedance value. In some embodiments, one of the first sensor array or the second sensor array is supported by an article of clothing and secured against a skin surface of the patient. In some embodiments, the article of clothing includes one of a belt, T-shirt, pants, or underwear. In some embodiments, the bladder volume measuring device further includes one of an ultrasound transducer or an optical laser sensor configured to measure a volume of fluid within the bladder. In some embodiments, the bladder volume measuring device further includes a computing device communicatively coupled thereto, the computing device also communicatively coupled to one of a network or an electronic health record system.

Also disclosed is a method of measuring a volume of fluid within a bladder of a patient including, securing an article of clothing about a torso, the article of clothing having a sensor disposed on an inner surface thereof, engaging the sensor with a skin surface of the patient, measuring an electrical impedance value for a bladder of the patient, and determining a volume of fluid disposed within the bladder using bio-impedance spectroscopy.

In some embodiments, the article of clothing includes one of a belt, T-shirt, pants, or underwear. In some embodiments, the method further includes providing an excitation signal from the sensor, the sensor being a first electrode, and detecting the excitation signal at a second electrode and determining the electrical impedance value. In some embodiments, the method further includes determining a total body water value of a body portion of the patient. In some embodiments, the method further includes determining a volume of fluid disposed within the bladder using one of an ultrasonic modality or an optical laser modality. In some embodiments, the method further includes communicating one of an electrical impedance value or a value for a volume of fluid disposed within the bladder to one of a computing device, network or an electrical health record system.

Also disclosed is a standing scale device including, a foot plate configured to support a patient standing thereon and including a first electrode, a handle supported by a post extending from the foot plate and configured to be grasped by both hands of the patient, the handle including a second electrode, and a TBW logic configured to measure an electrical impedance of the patient and determine a total body water value for the patient using bio-impedance spectroscopy.

In some embodiments, the standing scale device further includes a pressure sensor disposed in the foot plate and configured to determine a body weight measurement for the patient. In some embodiments, the standing scale device further includes a second sensor array having a third electrode and a fourth electrode configured to determine a bladder volume value for the patient. In some embodiments, the standing scale device further includes a communications logic configured to transmit the total body water value for the patient to one of a network or an electronic health record system.

Also disclosed is a total body water measuring device including, a first electrode configured contact a skin surface proximate an ankle of a patient, a second electrode configured contact a skin surface proximate a wrist of the patient, and a TBW logic configured to determine an electrical impedance value between the first electrode and the second electrode and determine a TBW value for the patient using bio-impedance spectroscopy.

In some embodiments, one of the first electrode or the second electrode is secured in place with a bracelet. One of the first electrode or the second electrode includes a coating disposed on a skin-facing surface thereof, the coating including one of a hydrogel or a urethane material. In some embodiments, the total body water measuring device further includes a second sensor array having a third electrode and a fourth electrode configured to detect a second electrical impedance value for the patient, the TBW logic configured to determine a bladder volume value from the second electrical impedance value. In some embodiments, the total body water measuring device further includes a communications logic configured to communicate a TBW value to one of a network or an electronic health record system.

Also disclosed is a method of measuring a total body water value for a patient including, coupling a first electrode with a first region of a patient, coupling a second electrode with a second region of a patient, measuring an electrical impedance value between the first electrode and the second electrode, and determining a total body water value for the patient using bio-impedance spectroscopy.

In some embodiments, the first region is one of a foot region or a hand region, and wherein the second region is one of a foot region or a hand region. One of the first electrode or the second electrode is secured in place with a bracelet. One of the first electrode or the second electrode includes a coating disposed on a skin-facing surface thereof, the coating including one of a hydrogel or a urethane material.

In some embodiments, the method further includes communicating a TBW value to one of a network or an electronic health record system. In some embodiments, the method further includes detecting a second electrical impedance value for the patient, and determining a bladder volume value from the second electrical impedance value.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1A shows a bladder volume monitoring ("BVM") device in an exemplary environment of use, in accordance with embodiments disclosed herein.

FIG. 1B shows a bladder volume monitoring ("BVM") device, in accordance with embodiments disclosed herein.

DESCRIPTION

Terminology

Figure 2:
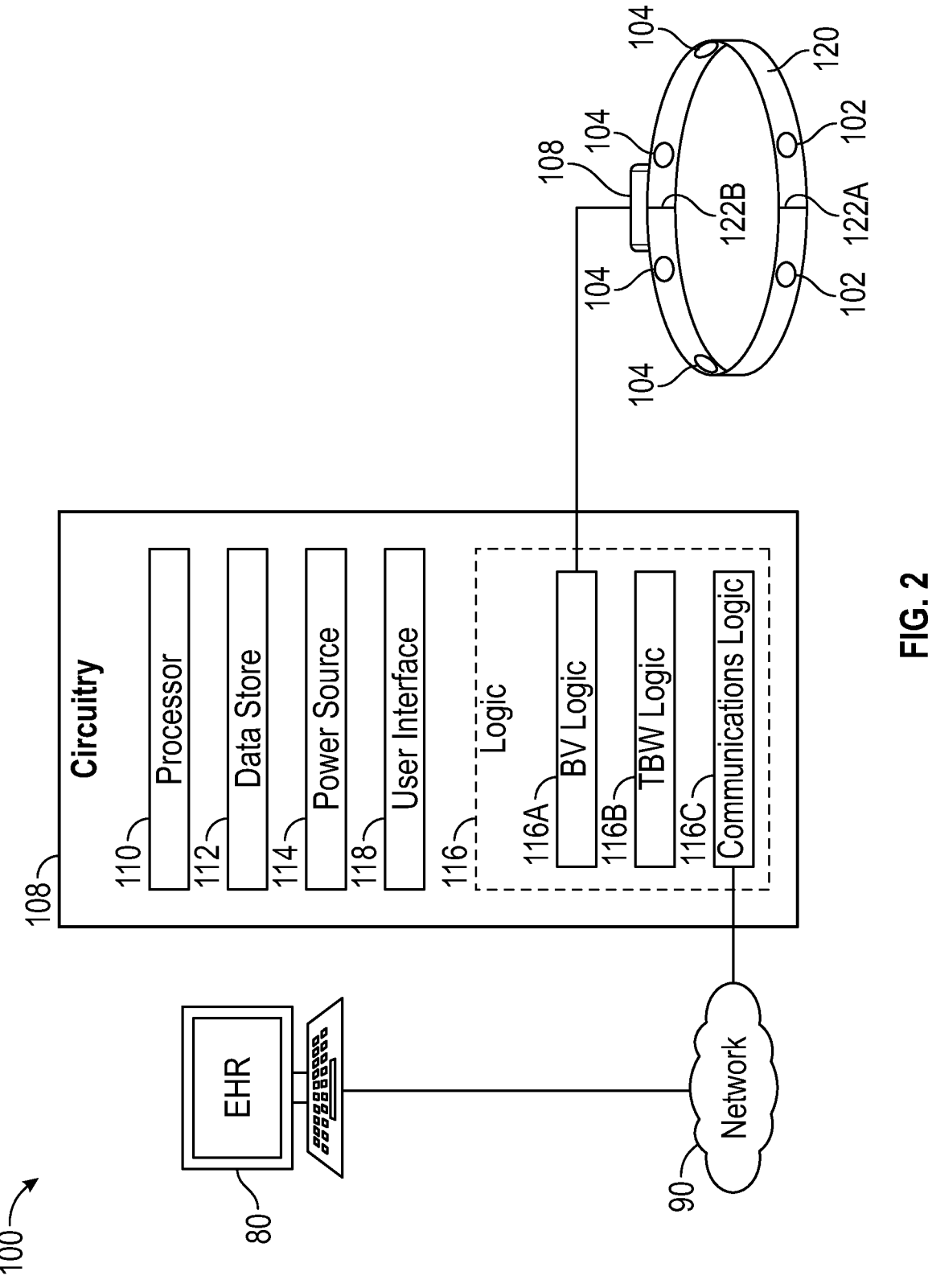
FIG. 2 shows a schematic view of the BVM device of FIG. 1B, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

As used herein, the term "communication" generally refers to related data that is received, transmitted, or exchanged within a communication session. The data may include a plurality of packets, where a "packet" broadly refers to a series of bits or bytes having a prescribed format. Alternatively, the data may include a collection of data that may take the form of an individual or a number of packets carrying related payloads, e.g., a single webpage received over a network. Further, as used herein, the terms "about," "approximately," or "substantially" for any numerical values or ranges indicate a suitable dimensional tolerance that allows the part or collection of components to function for its intended purpose as described herein.

In the following description, certain terminology is used to describe features of the invention. For example, in certain situations, the term "logic" is representative of hardware, firmware and/or software that is configured to perform one or more functions. As hardware, logic may include circuitry having data processing or storage functionality. Examples of such circuitry may include, but are not limited or restricted to a microprocessor, one or more processor cores, a programmable gate array, a microcontroller, a controller, an application specific integrated circuit ("ASIC"), wireless receiver, transmitter and/or transceiver circuitry, semiconductor memory, or combinatorial logic.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage. In an embodiment, the logic described herein may rely on heuristics, machine learning, artificial intelligence (A.I.), neural networks, or other data processing techniques to perform the described functionality.

The term "computing device" may be construed as electronics with data processing capabilities and/or a network interface capabilities, such as network connectivity to a physical or virtual network such as a public network (e.g., Internet), a private network (e.g., a wireless data telecommunication network, a local area network "LAN", etc.), a public cloud network, a virtual private cloud, of the like. Examples of a computing device may include, but are not limited or restricted to, the following: a server, an endpoint device (e.g., a laptop, a smartphone, a "wearable" device, a smartwatch, a tablet, a desktop or laptop computer, a netbook, or any general-purpose or special-purpose, user-controlled electronic device); a mainframe; a router; or the like.

The term "network" may include a public and/or private network based on wired or wireless interconnects and in a centralized or decentralized configuration. The networks may include, but are not limited or restricted to a Local Area Network (LAN), a Wireless Local Area Network (WLAN), a Virtual Private Network (VPN), intranet, internet, 'cloud' based network, or similar network configurations.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

The term "wireless" communication may include Bluetooth, WiFi, Near Field Communications (NFC), GSM, infrared, microwave, or the like.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Patient-Wearable Device for Non-Invasively Measuring Bladder Volume

FIGS. 1A-1B show a Bladder Volume Monitor ("BVM") device 100 in an exemplary environment of use. In an embodiment, the BVM 100 can be wearable and can non-invasively monitor a volume of fluid disposed within the bladder 12 of a patient 10, termed a "BV value." In an embodiment, the BVM 100 can include one or more of a first sensor array 102 and a second sensor array 104, which are in contact with a skin surface of the patient 10 and communicatively coupled, either wired or wirelessly, with circuitry 108. As used herein a "sensor array" can include one or more sensors configured to send and/or receive a signal output in a first modality and provide an output in a second modality. The first modality and the second modality can be the same or different. Exemplary modalities can include optical, electrical, acoustic, electro-impedance, or the like.

As shown in FIG. 2, the circuitry 108 can include one or more of a processor 110, a data store 112, a power source 114, one or more logic 116, a user interface 118, or combinations thereof. In an embodiment, the BVM device 100 can include a BV logic 116A communicatively coupled with one or more of the first sensors 102 and configured to accurately measure a BV value, i.e. a volume of fluid within the bladder 12 of a patient 10. In an embodiment, the BVM 100 can further include a communications logic 116C configured to communicatively couple with a network 90 and/or a remote computing device or database 80.

Exemplary networks 90 can include, for example, a local area network (LAN), hospital network, intranet, internet, "cloud" based network, or the like. Exemplary remote computing devices or databases 80 can include computing devices, mobile devices, "smart phones," tablets, laptops, mainframes, servers, electronic health record (EHR) systems, or the like. In an embodiment, the remote computing device 80 can include a handheld device or the like. The handheld device 80 can include a user interface 118 configured to allow a user or clinician to enter additional information. Exemplary additional information can include information about the patient (height, weight, age, gender, etc.), bladder voiding events (number, volume, date, time, etc.) volume of fluid intake (number, volume, date, time, etc.) by the patient 10, combinations thereof, or the like. In an embodiment, BVM 100 can retrieve this additional information from the remote database 80 or network 90 to further improve the accuracy of the of the BV logic 116A, as described in more detail herein.

In an embodiment, the first sensor 102 can be disposed on a skin surface of the patient 10 and secured in place by self-adhesive, adhesive tape, or the like. In an embodiment, the sensor 102 can be disposed on a belt 120, or similar article of clothing, configured to secure the sensor 102 against the skin surface of the patient 10. Exemplary articles of clothing can include belts, T-shirts, pants, underwear, or similar tight-fitting garments configured to hold the sensor securely against the skin surface of the patient 10.

As shown in FIGS. 1A-3, in an embodiment, the belt 120 can include a sensor 102 disposed on an inner surface thereof. The belt 120 can be worn about the waist of the patient 10 and urge the sensor 102 against the skin surface of the patient 10 to maintain contact therewith. In an embodiment, the sensor(s) 102 can be disposed within the lining of underwear, T-shirt, jogging pants, combinations thereof, or the like and configured to urge the sensor 102 against the skin surface of the patient 10, as described in more detail herein. Advantageously, the elastic nature of the article of clothing can ensure a comfortable contact between the sensor 102 and the skin surface. In an embodiment, the sensor 102 can be attached directly to the skin surface of the patient using a pressure-reactive adhesive, or the like.

In an embodiment, as shown in FIG. 2, one or more of components of the circuitry 108, e.g. the processor 110, data store 112, power source 114, or logic 116, can be disposed in a separate stand-alone unit from the belt 120 and sensor 102 assembly and communicatively coupled thereto, e.g. by wired or wireless communication. In an embodiment the circuitry 108, or one or more of components thereof, can be disposed within a stand-alone computing device, or "base station" disposed proximate the patient 10. In an embodiment the circuitry 108, or one or more of components thereof, can be disposed within a handheld device, "wearable" device (e.g. smart watch), tablet device, or laptop computer. In an embodiment, the circuitry 108 or one or more of components thereof, can be carried by the user in a waist bag or "fanny pack" and communicatively coupled, either wired or wirelessly, with the sensor 102 disposed in the belt 120 or article of clothing, as described herein. In an embodiment, the circuitry 108 can be detachable from the belt 120 and sensor 102 assembly. This allows the belt 120 and sensor 102 assembly to be washed separately, or to allow for disposal of old belt 120 and sensor 102 assemblies, while coupling a new belt 120 and sensor 102 assemblies to the BVM system 100 for that same patient or for a new patient.

Figure 3:
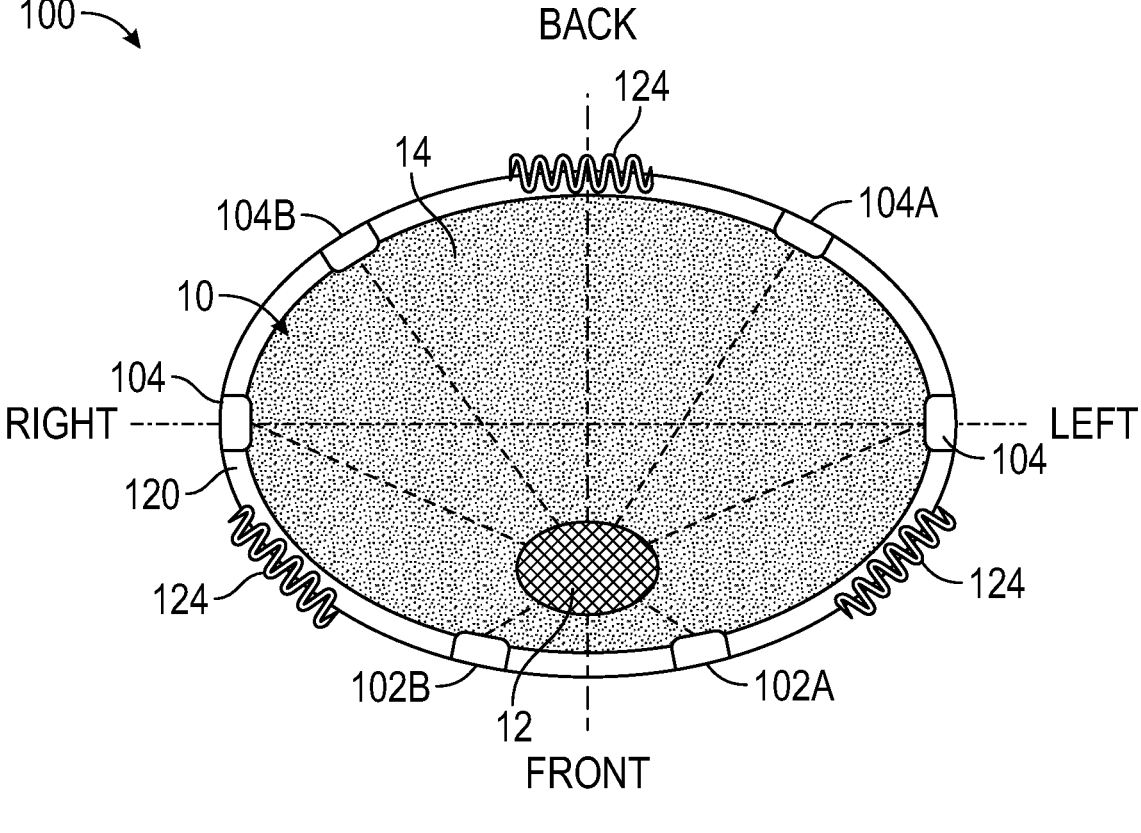
FIG. 3 shows a transverse cross-section view of a patient wearing a BVM device, in accordance with embodiments disclosed herein.

FIG. 3 shows a transverse cross-section view of a patient 10 wearing a BVM device 100 worn about the waist. In an embodiment, the belt 120 can fasten about the patient 10 with the fastening in the back to discourage removal of the device 100 or non-compliance from the patient 10. In an embodiment, the belt 120 can be adjustable to fit different sized patients 10. In an embodiment, the belt 120 can include one or more adjustable portions 124 disposed between the sensor(s) 102. The adjustable portions can be elasticated, slip lock buckle, ladder lock buckle, or the like. The adjustable portions 124 of the belt 120 can be configured to be adjusted to fit different sized patients, while maintaining the relative position of the sensors 102 about the waist of the patient 10.

In an embodiment, the belt 120 can include one or more markers 122 to facilitate alignment to anatomical features on the patient. For example, as shown in FIG. 2, a first marker 122A can align with a navel region, and/or a second marker 122B can align with a spine region of the patient 10. Advantageously, the marker(s) 122 can facilitate alignment of the sensor(s) 102 with correct areas of the patient 10.

In an embodiment, the first sensor array 102 can use one or more modalities to measure a volume of fluid within the bladder, and/or triangulate a location of the bladder 12. Advantageously, the BVM device 100 can triangulate a location of the bladder 12 to facilitate differentiating the fluid measurements of the bladder 12 from that of fluid measurements of the surrounding tissues, providing a more accurate measurement of fluid disposed within the bladder 12. Exemplary modalities can include ultrasound, laser, electrical impedance, or combinations thereof.

In an embodiment, the BVM 100 can use an electrical impedance modality to determine a location of the bladder 12 and/or a volume of fluid disposed within the bladder 12. The electrical impedance modality BVM device 100 can include a first sensor array 102 including a first electrode 102A configured to provide an excitation signal, and a second electrode 102B configured to detect the excitation signal of the first electrode 102A. The BVM 100 can determine a drop in signal strength between the first electrode 102A and the second electrode 102B to determine an electrical impedance of the body tissues disposed therebetween. In an embodiment, a hydrogel, urethane gel, or similar electrically conductive gel can be placed between the electrodes 102A, 102B and the skin surface to improve electrical conductivity therebetween. In an embodiment, the first sensor array 102 can include a single sensor 102A configured to both provide an excitation signal, and to detect the excitation signal. Similarly, a second sensor array 104 can include a single sensor 104A configured to both provide an excitation signal, and to detect the excitation signal.

In an embodiment, the first sensor array 102 can be disposed on the naval region of the patient, proximate the bladder 12, with a first electrode 102A disposed on a left side of the bladder 12 and the second electrode 102B disposed on the right side of the bladder 12. The excitation signal can travel from the first electrode 102A to the second electrode 102B, through the bladder 12. Different volumes of fluid within the bladder 12 can affect the electrical impedance of the excitation signal as it passes through the bladder 12.

In an embodiment, a second sensor array 104 can include a third electrode 104A and a fourth electrode 104B and can be communicatively coupled with a TBW logic 116B. The second sensor array 104 and TBW logic 116B can be configured to detect and determine one or both of a location of the bladder 12 and a volume of fluid within the body 14 of the patient 10, i.e. within tissues external to the bladder 12, or Total Body Water (TBW). The second sensor array 104 can be positioned on a different area of the body from the naval region. For example, as shown in FIG. 3, the second sensor array 104 can be positioned on a back portion of the patient 10 with the third electrode 104A and the fourth electrode 104B disposed either side of the spine. However, it will be appreciated that the second sensor array 104 can be positioned on other regions of the patient 10 without departing from the spirit of the invention. In an embodiment, the electrical impedance value determined by the second sensor array 104 and the TBW logic 116B can determine a total body water ("TBW") value of the patient 10.

Figure 10A:
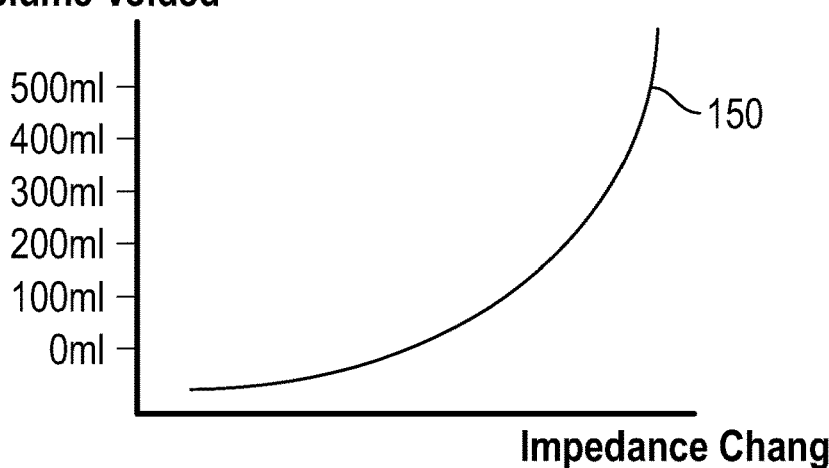
FIGS. 10A-10C show exemplary bio-impedance to bladder volume models, in accordance with embodiments disclosed herein.
Figure 10B:
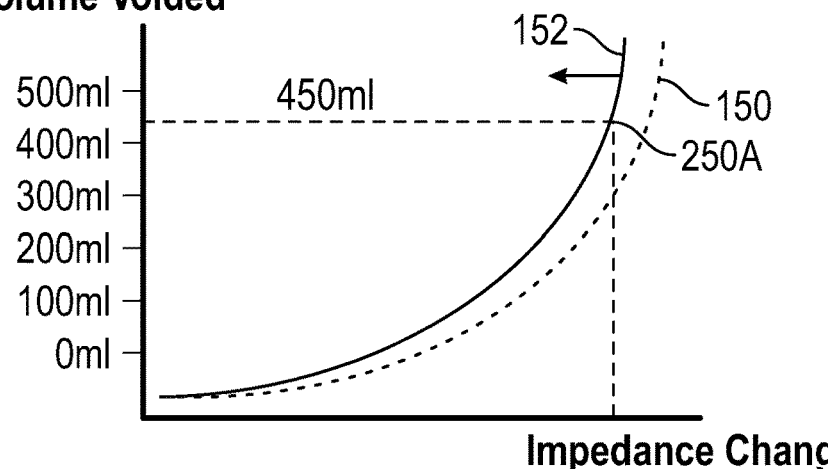
Figure 10C:
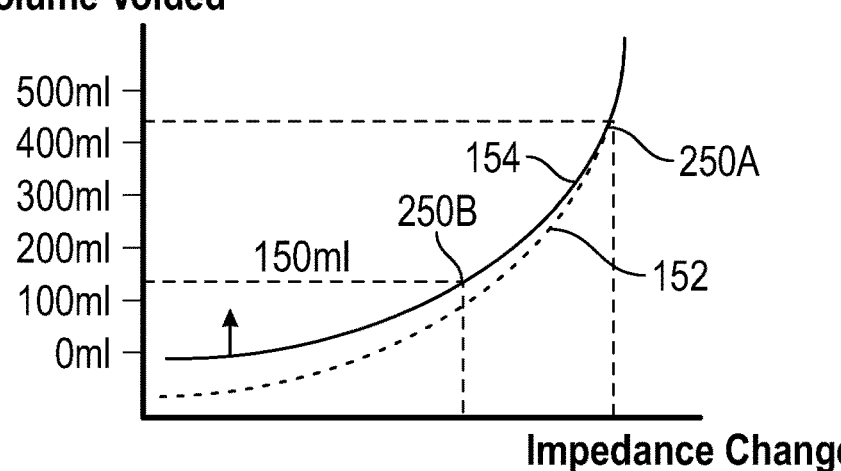

In an embodiment, the BVM 100 can detect both the amount of fluid accumulating within the bladder 12 as well as detecting any change in TBW of the patient 10. In an embodiment, the BVM 100 can use a bio-impedance spectroscopy ("BIS") model to determine one or both of a BV value and a TBW value from a bio-impedance value. The BVM 100 can be configured to modify the BIS model to "learn" the individual patient 10. The BVM 100 can use additional information from the target patient or aggregated data from one or more other patients different from the target patient. Additional information can be UO data entered to the BVM 100 by the user interface 118, automatic UO data from additional medical systems, fluid intake from additional medical systems, or the like, as described herein. FIGS. 10A-10C provide an exemplary BIS model such as a bladder volume model ("BV model") 150 configured to determine a BV value from an impedance measurement, as described in more detail herein. Similarly, a TBW model can determine a TBW value from an impedance value in a similar way. Further a lung fluid volume (LFV) model can determine a LFV value from an impedance value in a similar way, as described in more detail herein. In an embodiment, the BVM 100 can modify the BIS model to compensate for the TBW values of the tissues surrounding the bladder 12 and determine an accurate BV value. In an embodiment, the BV and TBW values can be immediately communicated to a network 80 or EHR 90 in real-time, for further analysis.

In an embodiment, the BVM 100 can retrieve additional information from one of the remote databases 80 or network 90 to further improve the accuracy of the BIS model determined by the BV logic 116A. In an embodiment, the remote database or computing device 80 can include a handheld device or the like. The handheld device 80 can include a user interface 118 configured to allow a patient 10, user, or clinician to enter additional information. Exemplary additional information can include information about the patient (height, weight, age, gender, etc.), bladder voiding event (number, volume, date, time, etc.) volume of fluid intake (number, volume, date, time, etc.) by the patient 10, combinations thereof, or the like, as described herein.

Advantageously, the BVM 100 can monitor and communicate changes in BV values, TBW values, or fluid intake values for a patient 10 over time. Such data can be essential to clinicians, for example, in determining if diuretic treatments are taking effect in HF or similar patients. Further, the BIS model (e.g. the BV model 150) used by the BVM 100 can adapt to different body compositions for different patients 10. This can be of particular importance when measuring bladder volume in HF or similar patients that may have atypical body morphology and atypical body composition. To note, some BV and TBW measuring systems rely on bio-impedance analysis ("BIA") that requires predetermined assumptions that a patient has a "normal" body morphology and body compositions. However, these assumptions may be less applicable to patients in critical care situations leading less accurate results.

In an embodiment, the BVM 100 can use an ultrasonic acoustic modality to triangulate a location of the bladder 12, and determine a volume of fluid disposed within the bladder 12. The ultrasonic modality BVM 100 can include a first transducer 102A and a second transducer 102B, configured to emit an ultrasonic signal into the patient 10 and detect a reflected ultrasonic signal. In an embodiment, the transducer 102A may be a transducer array that both emits and detects the reflected ultrasonic signal. In an embodiment, a hydrogel, urethane gel, or similar acoustically conductive gel can be placed between the sensor 102 and the skin surface to improve acoustic conductance therebetween.

The ultrasonic modality BVM 100 can detect a change density of the sub-cutaneous tissues proximate the first sensor 102A and the second sensor 102B to triangulate the location and dimensions of the bladder 12. Further, the change in reflected signal can further determine a volume of fluid within the bladder 12. For example, where the bladder 12 has relatively little fluid, a reflected ultrasonic signal will show little or no difference relative to the surrounding tissues. Where the bladder 12 is relatively full of fluid, a reflected signal will present greater differences relative to the surrounding tissues allowing for approximation of bladder volume. Worded differently, bladder ultrasound volumes are based on edge detection where the ultrasound determines a change in signal reflection to determine a bladder wall/urine interface. A three-dimensional volume model is then computed to estimate the volume of fluid in the bladder.

In an embodiment, the ultrasound modality BVM 100 can include a first array of transducers 102 and a second array of transducers 104, each configured to emit an ultrasonic signal into the patient 10 and detect a reflected ultrasonic signal. The ultrasound modality BVM 100 can measure the reflected signals from each of the first array of transducers 102 and the second array of transducers 104 to further increase the accuracy of triangulating the position of the bladder 12 and determining its dimensions and volume.

In an embodiment, one or more sensors 102 can employ an optical modality to determine one of a location of the bladder 12 or a volume of fluid therein. For example, the first sensor array 102A, 102B can direct a laser optical signal into the patient 10 and detect a reflected optical signal to determine one of a location of the bladder 12 or a volume of fluid therein. In an embodiment, a plurality of optical sensor arrays 102, 104 can improve the accuracy of the location bladder 12, and the volume of fluid within the bladder 12.

Figure 4:
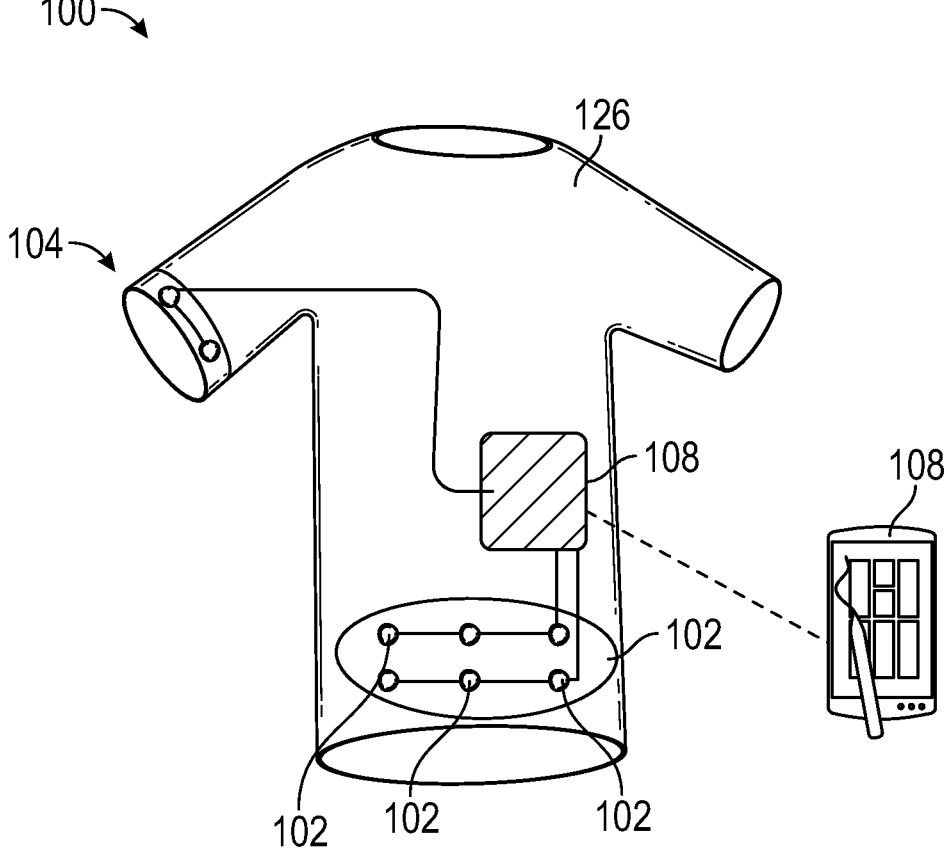
FIG. 4 shows a wearable BVM device, in accordance with embodiments disclosed herein.

As shown in FIG. 4, in an embodiment, the BVM 100 can be included in an article of clothing, for example a T-shirt 126. As will be appreciated the T-shirt 126 is exemplary and embodiments of the invention can be used with various articles of clothing including belts, T-shirts, pants, underwear, or similar tight fitting garments configured to hold one or both of the first sensor array 102 and the second sensor array 104 securely against the skin surface of the patient. One or both of the first sensor array 102 and the second sensor array 104 can be disposed within a lining of the T-shirt 126 and the T-shirt 126 can be formed of a tight fitting material to ensure the sensors are secured against the skin surface of the patient 10.

In an embodiment, the T-shirt 126 can include a first sensor array 102 disposed about the waist portion of T-shirt 126 and configured to determine a BV value, as described herein. The first sensor array 102 can include one or more sensors that can use the same or different modalities, as described herein. For example, the first sensor array 102 can include six sensors disposed about the waist portion of the T-shirt 126 and configured to contact a skin surface of a patient 10 around the area of the bladder 12, when the T-shirt 126 is worn by the patient 10. Each of the six sensors can use the same or different modalities to determine a BV value.

In an embodiment, the T-shirt 126 can include a second sensor array 104 including one or more sensors that can use the same or different modalities, as described herein. The second sensor array 104 can be disposed on a different portion of the T-shirt 126, for example an arm portion and can be configured to determine a TBW value for the patient 10. Advantageously, the second sensor array 104 can be disposed in a spaced apart relationship from the first sensor array 102 to distinguish BV data from TBW data.

In an embodiment, the T-shirt 126 can further include one or more components of the BVM 100 or circuitry 108, for example, the processor 110, data store 112, power source 114, one or more logic 116, user interface 118, or combinations thereof. These components can be sewn into the lining of the T-shirt and can be communicatively coupled, either wired or wirelessly, with the first sensor array 102 or the second sensor array 104.

In an embodiment, one or more components of the BVM 100 or circuitry 108 can be disposed remotely from the T-shirt 126 and wirelessly coupled thereto. For example, one of the first sensor array 102 or the second sensor array 104 can be communicatively coupled with a computing device, handheld device, "base station," or similar device that can include one or more components of the BVM 100 or circuitry 108, i.e. the processor 110, data store 112, power source 114, one or more logic 116, user interface 118, or combinations thereof.

Self-Learning, Non-Invasive Bladder Monitoring System

Figure 5:
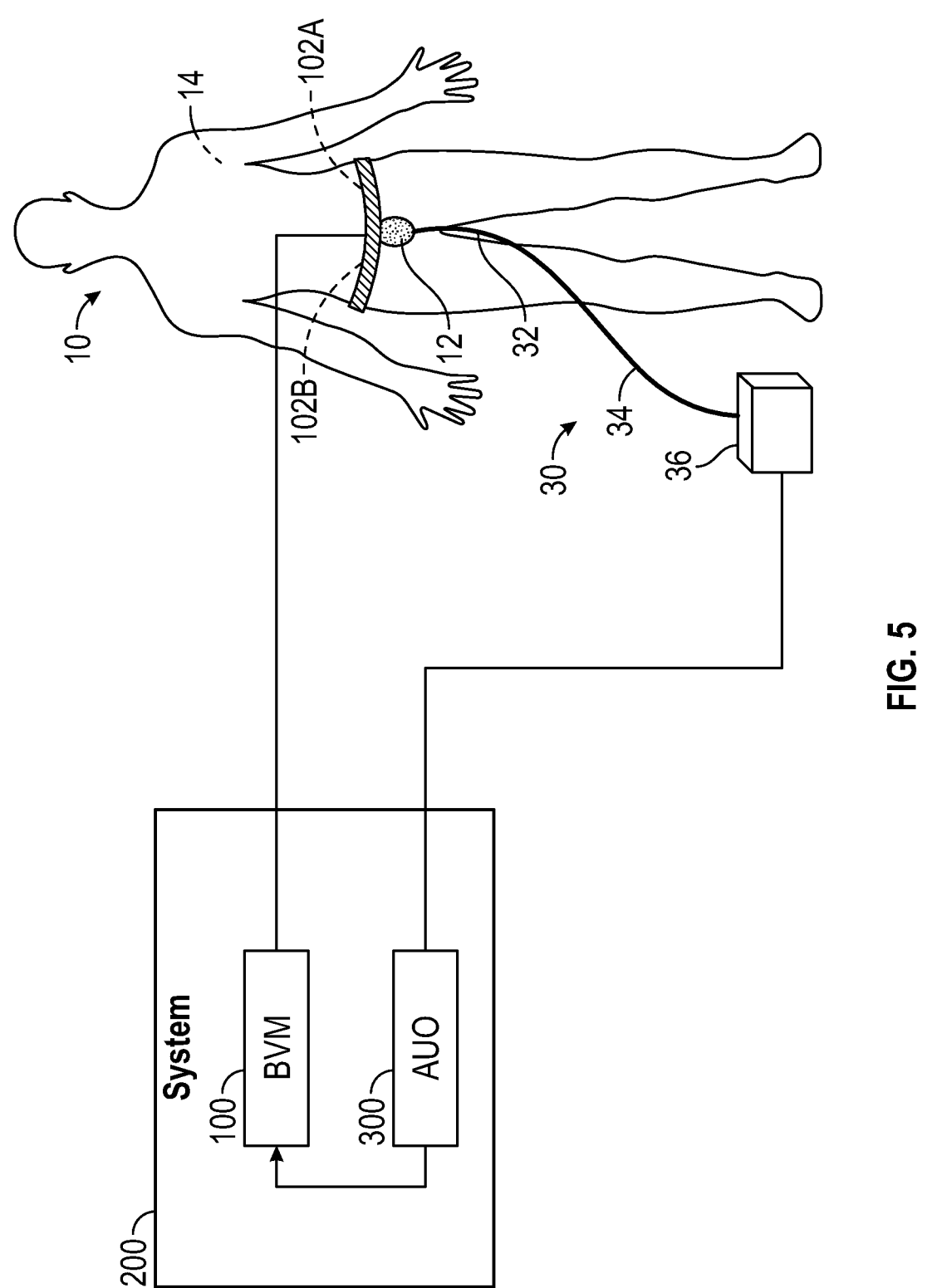
FIG. 5 shows a schematic view of a self-learning, non-invasive bladder monitoring system in an exemplary environment of use, in accordance with embodiments disclosed herein.

FIG. 5 shows an exemplary self-learning, non-invasive bladder monitoring system ("system") 200 including a bladder volume monitoring system ("BVM") 100 and a training system, such as an automatic urine output training system ("AUO") 300. As shown, the AUO training system 300 can be coupled directly with the system 200 by either wired or wireless communication. In an embodiment, the AUO training system 300 can be indirectly coupled with the system 200 by way of one or both of the network 90 and remote computing device 80.

The system 200 can be configured to non-invasively detect a volume of fluid within the bladder 12 of a patient 10. The system 200 can use one or more modalities to determine the bladder volume ("BV") metric for the patient 10. Exemplary modalities can include electrical impedance, ultrasound, optical modalities, or combinations thereof, as described herein. Further the system 200 can determine a total body water ("TBW") metric for the patient 10, as described herein. In an embodiment, the system 200 can use the TBW values to provide improved accuracy of the BV values for the patient 10.

In an embodiment, the system 200 can also include a training system configured to independently verify a volume of fluid within the bladder 12 and "train" the BVM 100 to improve accuracy. In an embodiment, the training system can include the automatic urine output training system ("AUO") 300 configured to automatically determine a volume of fluid voided by the patient 10 (urine output value, or "UO" value). The system 200 can use the AUO values to modify a bio-impedance to bladder volume model ("BV model") 150 to "learn" the specific patient 10 and provide improved, personalized BV and/or TBW data. Other training systems can include an ultrasound based training system 400 or a pressure based training system 500, as described in more detail herein.

In an embodiment, once the BVM 100 has been trained to the specific patient 10, the training system 300, 400, 500 can be detached from the system 200 and the system 200 can record BV and/or TBW data non-invasively. In an embodiment, one or more of the training systems 300, 400, 500 can be communicatively coupled with the system 200 directly by wired or wireless communications. In an embodiment, one or more of the training systems 300, 400, 500 can be communicatively coupled with the system 200 indirectly by way of the network 90 and/or remote computing device 80. BV and/or TBW data can also be communicated to a network 90 and/or remote database or remote computing device 80 (e.g. electronic health record system, "ERR") for further analysis. Patient specific BV or TBW data can be important in evaluating renal function and determining the efficacy of diuretic treatment of complex patients. Exemplary complex patients can include HF patients presenting with various comorbidities or atypical body composition.

Figure 6:
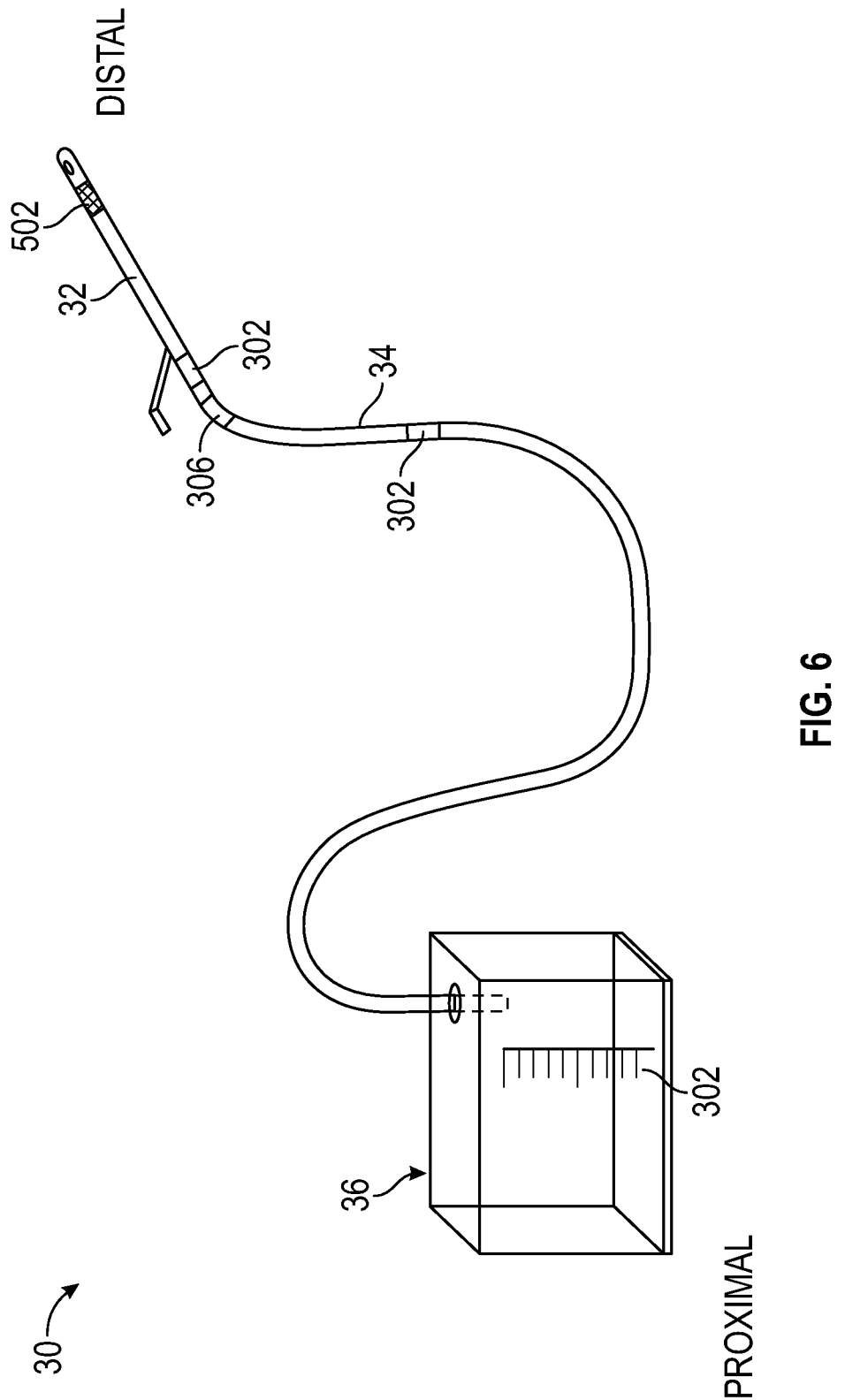
FIG. 6 shows an exemplary urine collection system, in accordance with embodiments disclosed herein.

FIG. 6 shows an exemplary urine collection system 30 including a catheter 32, a drainage tube 34, and a collection container 36. The catheter 32 can be a Foley catheter, indwelling urinary catheter, balloon catheter, non-balloon catheter, suprapubic catheter, ureteral catheter, nephrostomy catheter, or similar device configured to drain a fluid from a patient, for example to drain urine from a bladder 12 of the patient 10. The drainage tube 34 can be configured to drain a fluid from the catheter 32 to the collection container 36.

Figure 7:
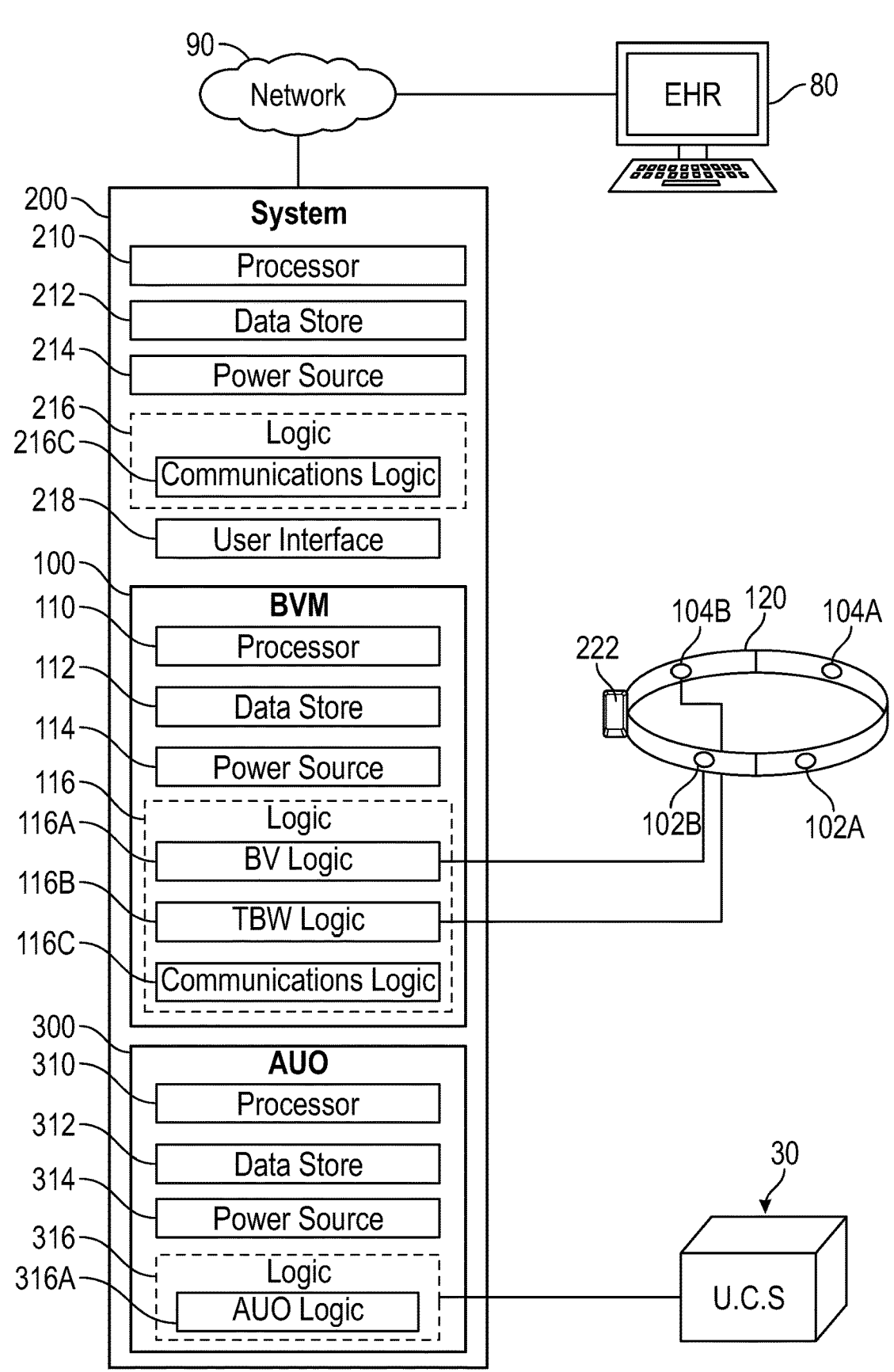
FIG. 7 shows a schematic view of a self-learning, non-invasive bladder monitoring system including an automatic urine output based training system, in accordance with embodiments disclosed herein.

FIG. 7 shows a schematic view of the system 200 including the BVM 100 and an AUO based training system 300. In an embodiment, the system 200 can include a processor 210, a data store 212, a power source 214, one or more logic 216 (e.g. communications logic 216C), a user interface 218, or combinations thereof. In an embodiment, the BVM 100 can include a processor 110, a data store 112, a power source 114, or combinations thereof. The processor 110, data store 112, or power source 114 of the BVM 100 can be in addition to, or in place of, the processor 210, data store 212, or power source 214 of the system 200. As such the BVM 100 can be a stand-alone unit communicatively coupled to the system 200 and optionally detachable therefrom. Alternatively, the BVM 100, or components thereof, can be integrated with the system 200 as a single unit.

In an embodiment, the BVM 100 can further include one or more logic 116 and one or more sensor arrays, e.g. a first sensor array 102, a second sensor array 104 communicatively coupled thereto, and configured to detect and determine one of a bladder volume ("BV") value, a Total Body Water ("TBW") value, or both. In an embodiment the BVM 100 can measure one of the BV or TBW values using one of bio-impedance analysis ("BIA"), bio-impedance spectroscopy ("BIS"), bio-impedance plethysmography ("BIP"), or bio-impedance tomography ("BIT"). However, it will be appreciated that other methods of measuring BV or TBW values using electrical impedance, ultrasound, or optical (e.g. laser) modalities are also contemplated to fall within the scope of the present invention.

In an embodiment, BIS measures a water content for the patient 10 using electrical impedance. An excitation signal is provided at a first sensor, e.g. a first electrode 102A and detected at a second sensor, e.g. a second electrode 102B. The first electrode 102A and the second electrode 102B can be positioned across a portion of the patient 10 that is to be measured. The amount of impedance to the signal between the first electrode 102A and the second electrode 102B can be correlated to the amount of water content. To note, bio-impedance spectroscopy differs from bio-impedance analysis ("BIA"). BIA relies on generalizations in patient body shape, size, composition, and demographic. These generalizations can be less applicable to critical care patients, e.g. HF patients or hypervolemic patients, who already differ from the general population by nature of their condition.

In an embodiment, a first sensor array 102 including a first electrode 102A and a second electrode 102B, can be placed on the abdomen of the patient 10 on either side of the navel area. The first sensor array 102 can be communicatively coupled, either wired or wirelessly, with a BV logic 116A and configured to send and receive an electrical signal to determine an impedance of the bladder region 12 of the patient 10. As such, the BV logic 116A can determine a volume of fluid within the bladder 12 for a patient 10.

In an embodiment, a second sensor array 104 can include a third electrode 104A and a fourth electrode 104B, and can be placed on a body portion 14 of the patient 10, for example on a back of the patient, either side of the spine. The second sensor array 104 can be communicatively coupled, either wired or wirelessly, with a TBW logic 116B and configured to send and receive an electrical signal to determine an impedance of the body portion 14 of the patient 10. As such, the TBW logic 116B can determine a volume of fluid within the tissues of the patient 10.

In an embodiment, one or both of the first sensor array 102 and the second sensor array 104 can be in contact with the patient's skin to measure an electrical impedance. In an embodiment, one or both of the first sensor array 102 and the second sensor array 104 can be adhered to the skin of the patient 10. In an embodiment, one or both of the first sensor array 102 and the second sensor array 104 can be disposed on a belt 120 secured about the patient's torso and configured to secure one or both of the first sensor array 102 and the second sensor array 104 to a skin surface.

It is important to note that different patients can have different amounts of body tissue disposed between the skin surface and the bladder 12. The water content of the tissues disposed between the skin surface and the bladder 12 can affect the BV measurements of the first sensor array 102. As such, the BVM 100 can include two sensor arrays 102, 104. The first sensor array 102 can be disposed over the bladder 12 and configured to measure a BV metric. The second sensor array 104 can be disposed over a different portion of the patient, e.g. body portion 14, and can be configured to determine a TBW metric for the patient 10. The BVM 100 can then determine an accurate BV by compensating for the TBW of the tissues disposed between the skin surface and the bladder 12. As such the BVM 100 can accurately determine the BV of the patient 10.

In an embodiment, the system 200 can monitor one of the BV values or TBW values for the patient 10, over a period of time. In an embodiment, the system 200 can further include a date/time stamp to the BV values, TBW values, or urine output (UO) values recorded by the system 200, as described herein. As such, the system 200 can then align these events with additional data entered to the system 200, either directly by way of the user interface 118, or indirectly from the network 90 or remote database 80. This information can be stored locally, e.g. data store 114 or data store 214, or communicated with a network 90 or remote database 80, such as a hospital network or an electronic health record ("EHR") system. It will be appreciated that exemplary networks 90 and remote databases 80 can include one or more computing devices including electronics with data processing capabilities and/or a network interface capabilities, such as intranets, internets, "cloud" based networks, servers, hospital networks, EHR systems, and the like.

In an embodiment, the system 200 can include a user interface 218, configured to receive additional information. Exemplary information can include, but not limited to, patient variables such as gender, age, height, weight, anatomical measurements, body composition, body mass index ("BMI"), measured post-void residual volume, date/time of voiding events, voided urine output volumes, adjustments to automatic urine output volumes, or the like. These variables can be entered by the clinician, patient, or automatically queried from a remote database 80, by way of a network 90, (e.g. EHR, "cloud" based network, intranet, internet, LAN, or the like).

In an embodiment, as shown in FIGS. 10A-10C, the system 200 can apply the bio-impedance measurements to a bio-impedance to bladder volume model ("BV model") 150 to determine a volume of fluid within the bladder 12, i.e. a BV value. FIG. 10A shows an exemplary BV model 150 which shows a correlation between the change in bio-impedance relative to the volume of fluid within the bladder 12. To note, the BV model 150 shown is a highly simplified example for ease of explanation, and as will be appreciated, the BV model may be linear, logarithmic, polynomial, multidimensional, time-variant, and/or can include one or more inflexion points.

In an embodiment, a TBW value for a patient can vary greatly between individuals which in turn can affect a BV metric from the first sensor array 102. As such, the system can monitor the TBW value, or changes thereof, for the patient 10 and modify the BV model 150 to accommodate these changes. Advantageously, the system 200 can monitor one of the BV and TBW values for the patient 10 over a period of time to determine the efficacy of diuretic treatments for the patient. In an embodiment, the BV logic 116 can continuously measure bio-impedance to determine changes in bladder volume, either through steady accumulation over time or by a sudden drop in bladder volume, indicating a bladder voiding event. In an embodiment, the BV logic 116 can determine changes in bladder volume and differentiate these from other artifacts, such as patient movement or patient position (sitting, standing, walking, lying down, etc.)

In an embodiment, the system 200 can include an accelerometer 222, gyroscope, or the like, configured to detect a speed, direction, or change in movement of the patient 10. The system 200 can detect movement of patient 10 to differentiate impedance changes that originate from redistribution and orientation of patient tissue or organs, fluid movement within the bladder, or geometric bladder shape changes due to patient position, from that of impedance changes due to bladder voiding events. For example, in females, the position of the uterus typically results in requiring some compensation mechanisms relative to ultrasound bladder scanning and/or bioimpedance measurements.

In an embodiment, the first sensor array 102 can be configured to detect relaxation of the urinary sphincter muscle and/or contraction of a detrusor muscle by way of surface electromyography. The BVM 100 can then directly detect when the muscles of the bladder 12 are contracting for a voiding event and the system 200 can record these events. As such the BVM 100 can further differentiate changes in BV impedance that occur due to movement of the patient 10 or other artifacts (e.g. movement of a sensor or sensor array), from those associated with a bladder voiding event.

Training System

In an embodiment, the system 200 can further include an Automatic Urine Output (AUO) based training system 300 configured to automatically measure a volume of urine voided by the patient 10. The urine output volume can be used to calibrate or "train" the BVM 100, or logic 116 included therein, to provide an accurate BV measurements for each individual patient 10.

In an embodiment, the AUO 300 can include a processor 310, a data store 312, a power source 314, or combinations thereof. The processor 310, data store 312 or power source 314 can be in addition to, or in place of, the processor 210, data store 212, or power source 214 of the system 200. As such the AUO 300 can be a stand-alone unit communicatively coupled to the system 200 and optionally detachable therefrom. Alternatively, the AUO 300, or components thereof, can be integrated with the system 200 as a single unit.

In an embodiment, the AUO 300 can further include one or more logic 316 (e.g. AUO logic 316A) and one or more sensors 302 configured to detect a volume of fluid voided from the bladder 12. In an embodiment, the sensor 302 can be coupled with the catheter 32 or with a drainage tube 34, and configured to measure a volume of fluid passing therethrough. In an embodiment the sensor 302 can be coupled with a collection container 36 and configured to measure a volume of fluid received therein.

BV Model Training

As shown in FIGS. 10A-10C, the system 200 can modify, or calibrate, the impedance measurements to the bladder volume model ("By model") 150 based on the urine output measurements from the AUO 300, or from patient- or clinician-entered measurements from actual voided amounts, or from other devices such as urodynamic monitors, pressure sensors, or ultrasound bladder scanners, or the like, as described in more detail herein. For example, as shown in FIG. 10A, an initial BV model 150 can be provided by the system 200 and stored locally, e.g. on data store 112 or data store 212. In an embodiment, the initial BV model 150 can be provided to the system 200 from a remote database 80 and/or from network 90. In an embodiment, the initial BV model 150 can be derived by the system 200 from an aggregation of previous BV models from the patient or from different patients having similar patient variables (e.g. gender, age, height, weight, etc.) Some information about the patient 10 can be entered to the system 200 using a user interface 218. Exemplary information may include age, gender, height, weight, body mass index ("BMI"), health conditions, or the like. The system 200 can then aggregate previously trained BV models from other patients with similar information to the patient 10, to provide an initial BV model 150. The system 200 can then detect a bio-impedance value from the first sensor array 102 and predict a first BV value 250A using the initial BV model 150.

As shown in FIG. 10B, the system 200 can then compare the first BV value 250A with a first urine output measurement (e.g. 450 ml). The system 200, e.g. the BV logic, can then modify the initial BV model 150 to a second BV model 152, to improve accuracy. Subsequent bladder voiding events can further refine the BV model. For example, as shown in FIG. 10C, a second voiding event provided a second urine output measurement 250B, (e.g. 150 ml) which can then be used to further modify the trained BV model 152 to a third BV model 154. The system 200 can continue to modify the BV model on an iterative basis, improving the BV model with each subsequent bladder voiding event, to refine the patient's specific profile.

In an embodiment, the system 200 can go through a training period to "learn" or calibrate the system 200, to the specific patient 10 and to provide an accurate estimate of the patient's BV values based on the bio-impedance measurements. In an embodiment, the system 200 can go through a training period of a predetermined time window, or a predetermined number of bladder voiding events. In an embodiment, the system 200 can continue with a training period until a difference between the estimated BV value and the urine output (UO) metric falls below a threshold value. In an embodiment, the threshold value can be a predetermined value or can be derived by the system 200.

In an embodiment, once the system 200 has been "trained" to the patient, the AUO 300 training system and/or urine collection system 30 can be detached and removed. As such the system 200 can continue to measure the BV values for the patient 10 using the trained BV model 154. Advantageously, detaching the AUO training system 300 and urine collections system 30 can reduce the need for invasive urine management devices and also improve portability of the system 200 allowing the patient 10 improved freedom of movement. The system 200 can be contained within a portable pack worn by the patient 10 and allow the patient 10 improved freedom of movement.

In an embodiment, the trained BV model 154 can be used by the system 200 to provide improved accuracy on TBW values for the patient 10. As such, the system 200 can determine an accurate TBW for each individual patient 10. Advantageously, the system 200 can monitor the TBW values for the patient 10 and determine any changes in patient TBW indicating the patient's response to diuretic treatments, response to other therapies, or changes in the patient's condition. Such information can provide a faster and more accurate indication of a response to diuretic treatment than current methods of periodic body weight measurements or bladder voiding measurements. This can be of particular importance if the patient fails to respond to diuretic treatment, requiring alternative treatments to be quickly implemented.

In an embodiment, one of the BVM 100 or the AUO 300 can be a separate stand-alone system that is communicatively coupled with the system 200, either directly or indirectly by way of a network or the like. In an embodiment, one of the system 200, the BVM 100 or the AUO 300 can be a stand-alone "base station" disposed proximate to the patient, e.g. within the patient's room, and wirelessly coupled with one of the first sensor array 102, second sensor array 104, or the AUO sensor 302, disposed on the patient. As such, less equipment can be "worn" by the patient 10 improving patient comfort. In an embodiment, the system 200, or components thereof, can be disposed within a portable computing device, a monitor, a handheld device, a wearable device (e.g. smart watch, or the like), a laptop, a tablet device, or the like. In an embodiment, the system 200, or components thereof, can be disposed within a self-contained unit that is water resistant or waterproof and can allow for light bathing or showering without having to disengage the system 200 from the patient 10. In an embodiment, the system 200, or components thereof can be contained within a pouch, or "fanny pack" and can be worn by the user to facilitate carrying the system 200.

Advantageously, the electrical impedance sensors can be relatively inexpensive, light weight and require little pressure with the skin surface to establish a conductive contact therebetween, allowing a user to wear the sensors 102, 104, with little or no impact on their movements or comfort. Further, the sensors can be disposed of and the system 200 coupled with new sensors for each new patient, providing a more cost-effective system, especially for short term, critical care situations.

Advantageously, the system 200 including the BVM 100 and the AUO training system 300 allows for an automated, "closed loop" self-learning and calibration of the system 200 to each individual patient 10 allowing for increased accuracy in "complex" patients with comorbidities.

Bladder Training

When a patient 10 is catheterized for an extended period of time, a number of problems can occur. For example, the bladder 12 can lose elasticity and compliance leading to incontinence or urgency, or leading to other abnormal bladder and voiding function, after the catheter 32 is removed. Often the patient can have the sensation of a full bladder and the need to void, despite having only a relatively small volume of urine in the bladder. In an embodiment, the AUO logic 316A can be communicatively coupled with a valve 306 and can selectively open or close the valve 306 to control a fluid flow through the urine collection system 30. The valve 306 can be disposed in one of the lumen of the catheter 32, or the lumen of the drainage tube 34, or any appropriate location for controlling urine flow in the urine collection system 30. The AUO 300 can be configured to occlude the drainage lumen of the catheter 32 or the drainage tube 34 to allow urine to accumulate within the bladder 12. The AUO 300 can allow urine to accumulate until the bladder 12 is considered "full" i.e. the urine volume is at a percentage of total bladder capacity. The system 200 can measure a BV value of the bladder 12, as described herein, and can determine when the bladder 12 is sufficiently full to open the valve 306. The AUO logic 316A can then transition the valve 306 from the closed position to the open position to allow the patient 10 to void the bladder 12 before closing the valve 306 again ready for the next cycle of voiding.

The cyclical closing of the valve and accumulation of urine followed by a voiding event can maintain or retrain bladder elasticity, compliance and natural bladder function. Further the cyclical filling and voiding of the bladder 12 can further train the BV model 150 to determine a percentage accumulation of urine within the bladder 12, a percentage bladder volume where voiding is required, a volume of voided urine, and/or a residual volume of urine remaining within the bladder 12 after a voiding event. In an embodiment, the valve 306 can include a redundant pressure relief mechanism configured to open the valve and relieve pressure in the event of a failure in the pressure sensor, valve or logic controlling the valve. Advantageously, should the system 200 fail to open the valve 306 prior to a threshold value being reached, the valve 306 can include a fail-safe mechanism to open the valve 306 when the threshold value is reached and allow fluid to flow therethrough. This can prevent inadvertent trauma to the patient should the valve 306 fail to activate.

Safety Features of a Coordinated System

Advantageously, the system 200 including the BVM 100 and the AUO 300 can include one or more safety features. In an embodiment, the system 200 can provide one or more alerts to a clinician and can transmit the alerts either directly to the clinician from the system 200, or indirectly by way of a network 90 and/or to a remote computing device such as the EHR 80. The alert can be a visual, audible or tactile alert.

In an embodiment, where the AUO 300 sets the valve 306 to open and the BVM 100 subsequently determines little or no change in bladder volume, the system 200 can provide an alert to a clinician that an error has occurred, e.g. an occlusion in the urine collection system 30, a malfunction of the valve 306, or the like.

In an embodiment, the system 200 can determine when the bladder 12 is approaching a maximum bladder volume capacity, which may be uncomfortable for the patient 10 or is clinically unacceptable, and can provide an alert to a clinician. This can be of particular importance where patients are incapacitated and cannot indicate to a clinician the sensation of discomfort, and can result in trauma to the patient 10. For example, a major risk can be reflux into the ureter and pressure back-up to the kidneys resulting in hydronephrosis.

In an embodiment, the system 200 can determine when the bladder 12 is approaching a maximum or pre-determined bladder volume capacity and can provide an alert to a clinician in lieu of the clinician performing a scheduled bladder ultrasound scan to assess the need for intermittent catheterization. This can be of particular importance because it reduces the incidence of inefficient scanning (i.e. no need for intermittent catheterization) that is time-consuming for clinicians and disruptive for patients.

In an embodiment, the system 200 can determine when the bladder 12 is approaching a maximum or pre-determined bladder volume capacity and can provide an alert to a patient. This can be of particular importance for certain types of patients who are substantially independent but cannot sense bladder fullness such as spinal cord injury patients who rely on intermittent self-catheterization to empty their bladders. This may further reduce the incidence of unnecessary intermittent catheterizations and the associated risk of urethral trauma and infection.

In an embodiment, the system 200 can further include a pressure sensor 502 disposed at a tip of the catheter 32, within the patient bladder 12 to directly measure a bladder pressure of the patient, as described in more detail herein. In an embodiment, the pressure sensor 502 can be disposed within the lumen of the catheter 32, the lumen of the drainage tube 34, or within the collection container 36 and configured to measure a bladder pressure of the patient, as described in more detail herein. The system 200 can then determine a bladder pressure value of the patient and determine when a bladder pressure is approaching an uncomfortable, or clinically unacceptable, level. The system 200 can then provide an alert to the clinician or transition the valve 306 to the open position, to release the pressure.

System with Ultrasound Based Training System

Figure 8:
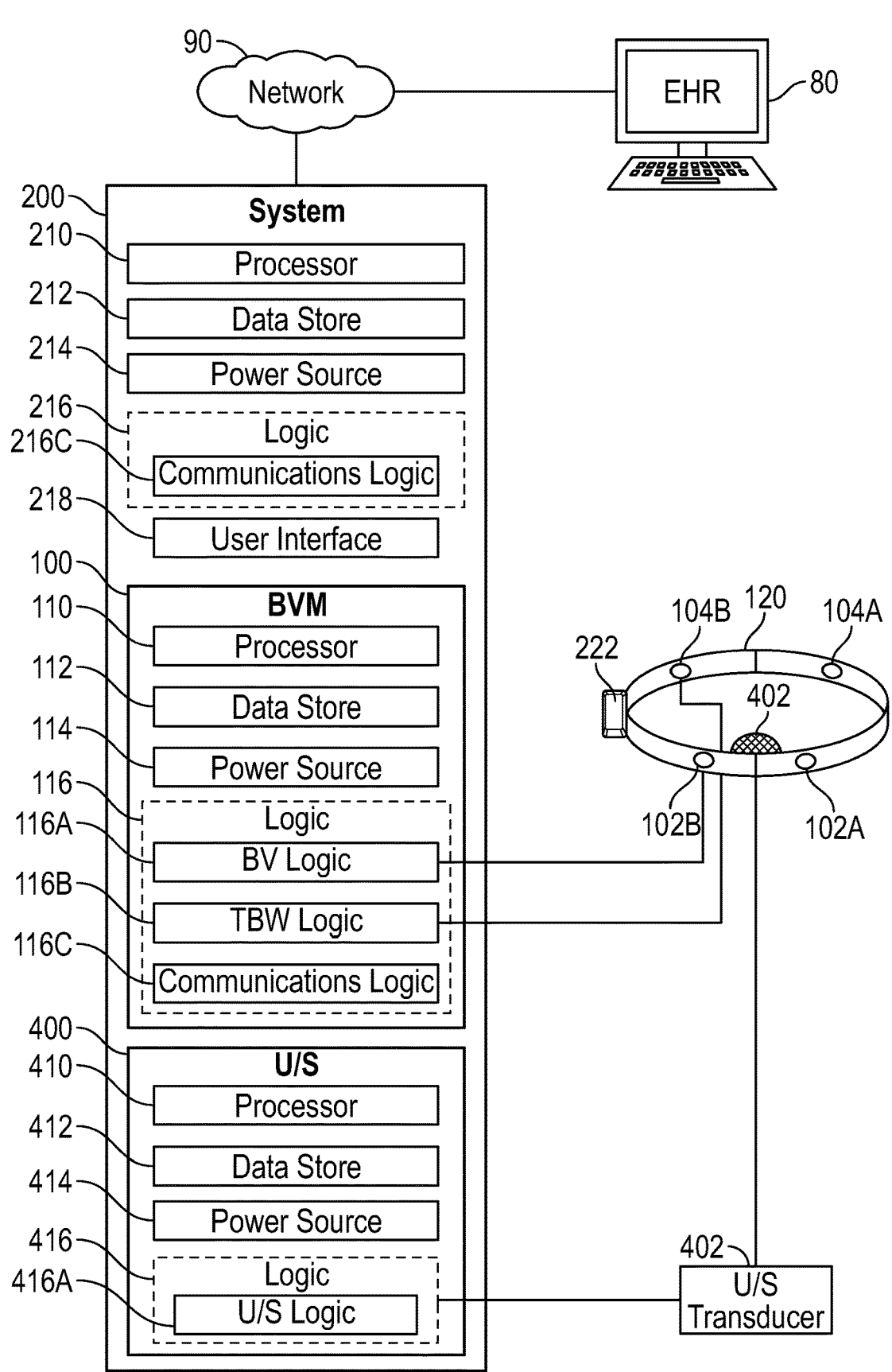
FIG. 8 shows a schematic view of a non-invasive bladder monitoring system including an ultrasound based training system, in accordance with embodiments disclosed herein.

As shown in FIG. 8, in an embodiment, the system 200 can include a BVM 100, as described herein, and an ultrasound based training system ("U/S system") 400 configured to train the BV model 150. The U/S system 400 can be configured to directly measure a volume of fluid within the bladder 12 using ultrasound. In an embodiment, the U/S system 400 can include a processor 410, data store 412, power source 414, or combinations thereof, in addition to, or in place of, the processor 210, data store 212, or power source 214 of the system 200.

In an embodiment, the U/S system 400 can further include one or more logic 416 (e.g. U/S logic 416A) communicatively coupled with an ultrasound transducer 402 and configured to provide an ultrasonic acoustic signal. The U/S logic 416A can be configured to detect a reflected ultrasonic signal and determine a volume of fluid within the bladder, (BV value) for either before or after a bladder voiding event. In an embodiment, the ultrasound transducer 402 can be held in place by a clinician to periodically measure a volume of fluid within the bladder 12 using a stand-alone, portable bladder scanner U/S system 400. This may be done before and after an intermittent catheterization procedure and may or may not also include measuring the volume of urine collected during that procedure. In an embodiment, the ultrasound transducer 402 can be secured to the abdomen, around the bladder area, or just above the pubic bone, with adhesive or the like. In an embodiment, the ultrasound transducer 402 can be disposed on an inner surface of the belt 120. The belt 120 can be configured to secure the transducer 402 to the abdomen, around the navel area. The belt 120 can be adjustable to maintain sufficient pressure between the transducer 402 and the skin surface to ensure a sufficient acoustic conductance therebetween. In an embodiment, a hydrogel, urethane gel, or similar ultrasonic conducting gel can be disposed between the transducer and the skin surface to further ensure sufficient acoustic conductance therebetween.

Advantageously, the U/S system 400 can calibrate or "train" the BVM system 200, as described herein, without having to collect and measure urine output from the patient 10. For example, where a patient 10 does not need to be catheterized using the urine collection system 30, the system 200 can still be trained to the individual patient 10 using the U/S training system 400 to train a BV model 150. This can avoid indwelling catheterization and allow the patient 10 an improved freedom of movement while still training the system 200, for example where the patient is semi-ambulatory.

In an embodiment, the U/S system 400 and the transducer 402 can be detachable from the system 200. As such, once the system 200 has been trained to the specific patient 10, the U/S system 400 can be removed, allowing the patient improved freedom of movement and improved comfort. The system 200 can then continue to monitor BV values with improved accuracy, as described herein.

In an embodiment, the system 200 can train the BVM 100 using one or more training systems, as described herein. For example, the BVM 200 can determine a BV value using electrical impedance and the BIS model (e.g. BV model 150) as described herein. The U/S system 400 can then confirm a BV value using the ultrasound modality and the system 200 can modify the BIS model if necessary. A patient 10 can then void the bladder and record the volume of voided fluid and enter the value to the system 200, e.g. by way of a user interface 218 or remote computing device 80. The U/S system 400 can then measure the residual fluid left in the bladder after the voiding event. The system 200 can then combine the voided bladder value, entered to the system 200, with the residual bladder volume value determined by the U/S system 400 to provide an accurate BV value and improve the accuracy of the BV model 150.

System with Internal Bladder Pressure Sensor Calibration

Figure 9:
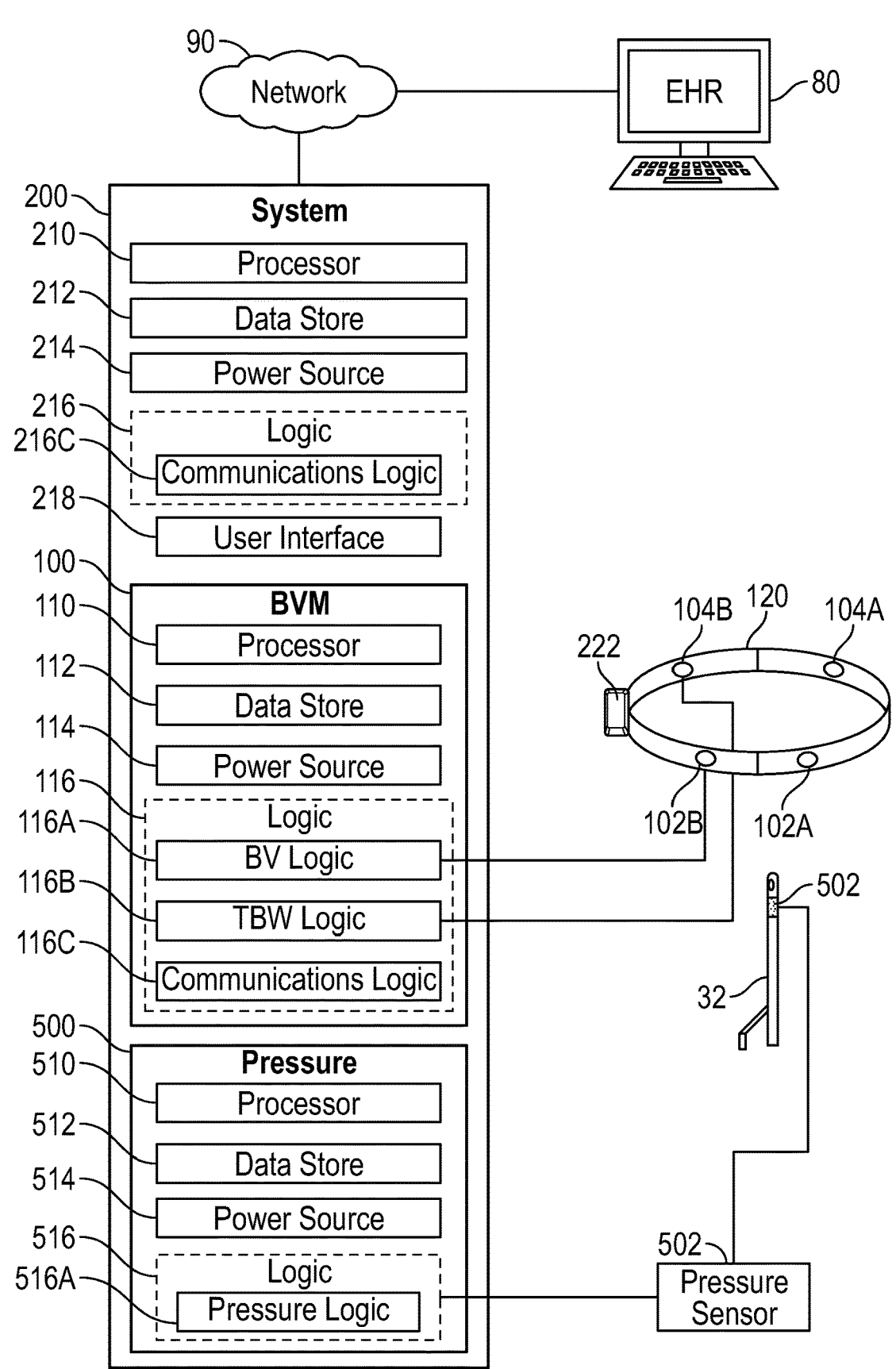
FIG. 9 shows a schematic view of a non-invasive bladder monitoring system including a pressure based training system, in accordance with embodiments disclosed herein.

As shown in FIG. 9, in an embodiment, the system 200 can include a BVM system 100, as described herein, and a bladder pressure training system 500, configured for training the BV model 150. The bladder pressure training system 500 can be configured to directly measure a volume of fluid within the bladder 12 by measuring a fluid pressure within the bladder 12.

In an embodiment the bladder pressure system 500 can include a processor 510, data store 512, power source 514, or combinations thereof in addition to, or in place of, the processor 210, data store 212, or power source 214 of the system 200, as described herein. In an embodiment, the bladder pressure system 500 can further include one or more logic 516 (e.g. pressure logic 516A) communicatively coupled with a pressure sensor 502. In an embodiment, the pressure sensor 502 can be disposed at a tip of the catheter 32, which can be disposed within the bladder 12 and can directly measure a pressure within the bladder 12 to determine a volume of urine therein.

Advantageously, for patients that already require to be catheterized, the pressure system 500 can calibrate or "train" the BVM system 200, as described herein, without having to collect and measure urine output from the patient 10. For example, urine output measurements can vary depending on the amount of residual urine left in the bladder after a bladder voiding event. These variations can add "noise" to the training data and may lead to a less accurate BV model. Further, collecting and measuring the urine that is voided from the bladder 12 can be messy and time consuming. For example, urine can be trapped in dependent loops within the drainage tube which can affect urine output measurements.

System with Intracorporeal Pressure Sensor Monitoring

In an embodiment, the system 200 can include a BVM system 100, as described herein, and an intracorporeal pressure monitoring system, e.g. bladder pressure system 500, configured for optimizing the BV model 150. The intracorporeal pressure monitoring system 500 can be configured to measure intra-abdominal pressure, and determine intracorporeal pressure changes that may affect the bioimpedance values and the determination of BV values or TBW values by the system 200. For example, abdominal compartment syndrome can cause changes in intra-abdominal pressure that can be detected by a pressure sensor disposed within the bladder, as described herein.

In an embodiment the intracorporeal pressure monitoring system 500 can include a processor 510, data store 512, power source 514, or combinations thereof in addition to, or in place of, the processor 210, data store 212, or power source 214 of the system 200, as described herein. In an embodiment, the intracorporeal pressure monitoring system 500 can further include one or more logic 516 communicatively coupled with a pressure sensor 502. In an embodiment, the pressure sensor 502 can be disposed at a tip of the catheter 32, which can be disposed within the bladder 12 and can directly measure a pressure within the bladder 12 to determine intra-abdominal pressure therein.

Advantageously, for patients that already require to be catheterized, the pressure system 500 can optimize the calibration or "training" the BVM system 200. For example, ascites and other conditions which result in fluid accumulation in the abdomen can affect the bio-impedance measurements. These variations can add "noise" to the training data and may lead to a less accurate BV model. Alerting the BVM system 200 to the likely presence of excess fluid, by way of intra-abdominal pressure measurement, will result in a more robust BV model 150.

Total Body Water and Bladder Volume Systems

Figure 11B:
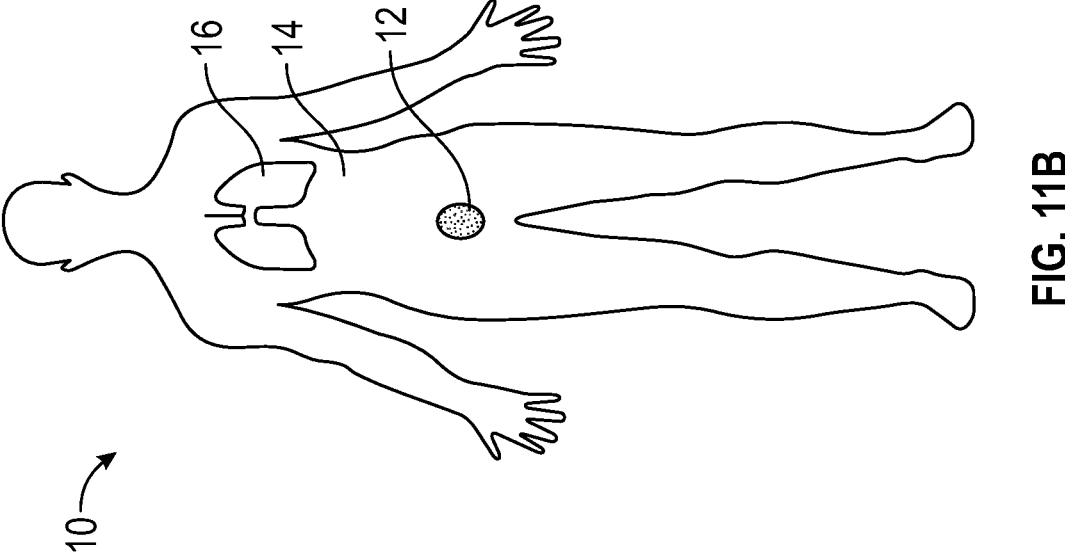
FIG. 11B shows an exemplary environment of use for a non-invasive TBW measuring device, in accordance with embodiments disclosed herein.
Figure 11A:
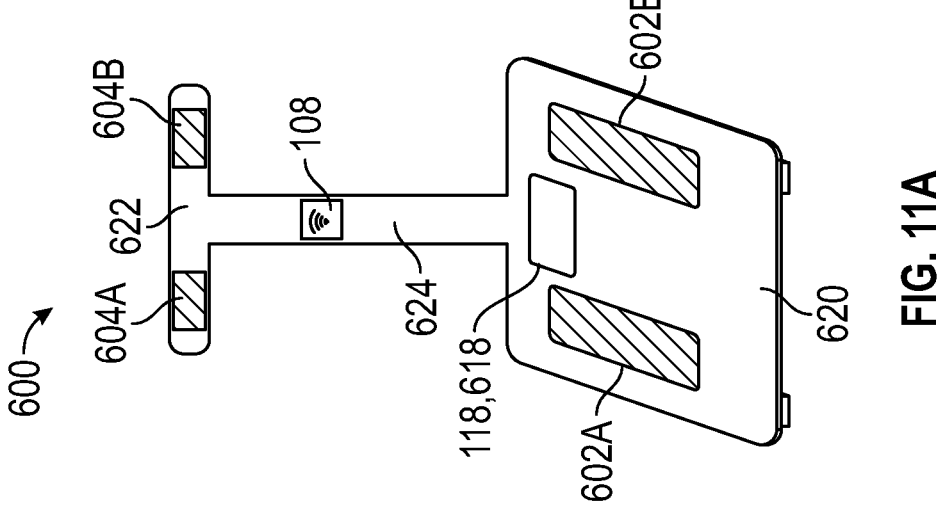
FIG. 11A shows a perspective view of a non-invasive TBW measuring device, in accordance with embodiments disclosed herein.

FIGS. 11A-11B show a free-standing, non-invasive TBW measuring device ("device") 600 configured to measure a TBW value for a patient 10 and/or a BV value for a bladder 12 of the patient 10. In an embodiment, the device 600 can be a "standing scale" device 600, including a foot plate 620 and a handle 622. The handle 622 can be supported by a post 624 extending from the foot plate 620. The foot plate 620 can be configured to support a patient 10 standing thereon. The handle 622 can be configured to be grasped by each hand of the patient when standing on the foot plate 620. The post 624 can support the handle 622 at an ergonomically comfortable height for the patient 10, e.g. between 2 feet and 4 feet from the foot plate 620. In an embodiment, the post 624 can be adjustable to allow the handle to be repositioned depending on the height of the patient 10.

In an embodiment, the foot plate 620 can include a first sensor array 602 including a left foot electrode 602A and a right foot electrode 602B. In an embodiment, the handle 622 can include a second sensor array 604 including a left hand electrode 604A and a right hand electrode 604B. In an embodiment, the foot plate 620 can further include a pressure sensor configured to determine a body weight value for the patient 10. The device 600 can further include a user interface 618 configured to display information or allow user to input information to the device 600. In an embodiment, the user interface 618 can be a touch screen, key pad, or the like.

Figure 12:
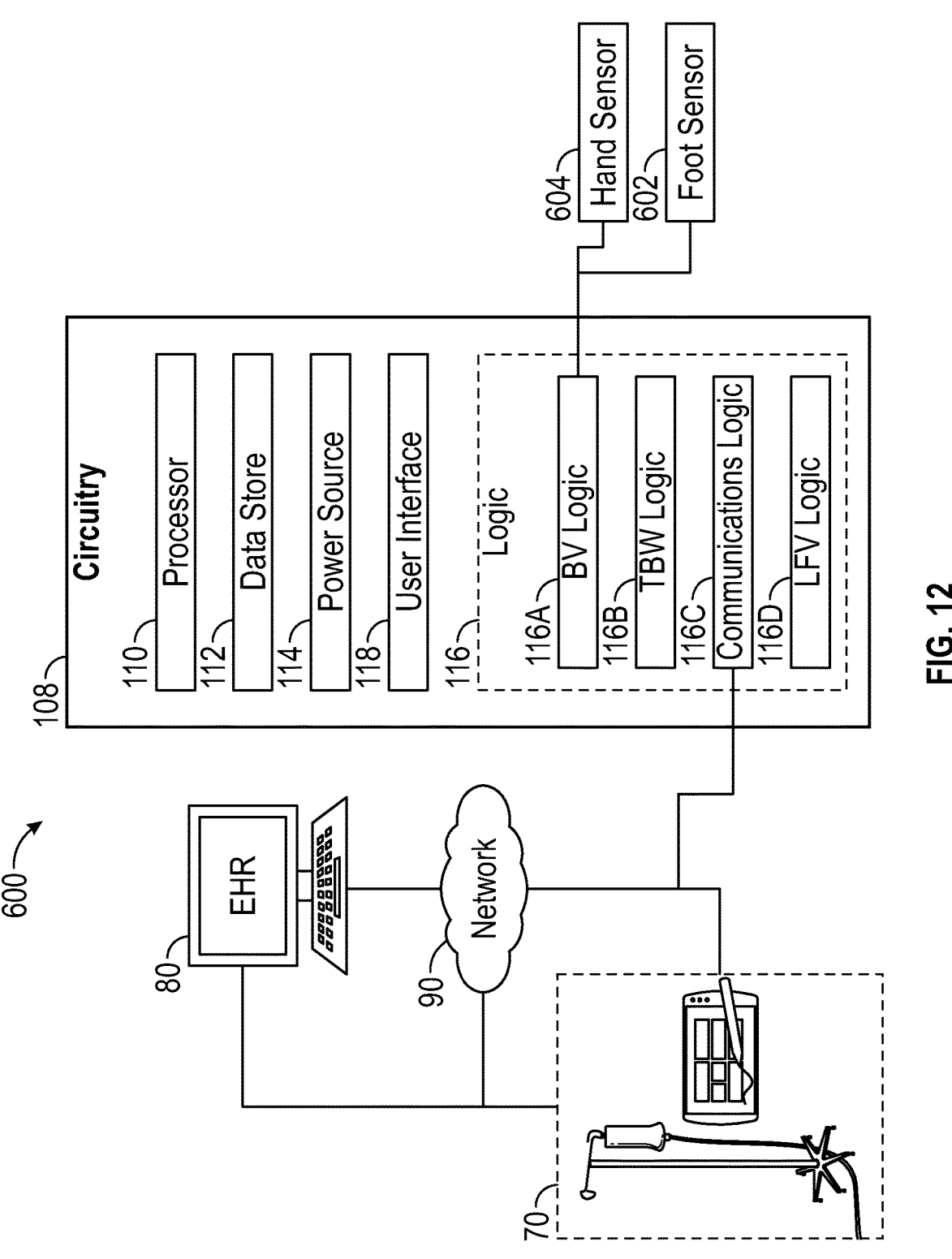
FIG. 12 shows a schematic view of a non-invasive TBW measuring device, in accordance with embodiments disclosed herein.

As shown in FIG. 12, in an embodiment, the device 600 can further include circuitry 108, which can include one or more of a processor 110, data store 112, power source 114, one or more logic 116 (e.g. BV logic 116A, TBW logic 116B, communications logic 116C, lung fluid volume ("LFV") logic 116D), a user interface 118 or combinations thereof, configured to measure a BV value or TBW value of the patient 10, as described herein. In an embodiment, the device 600 can be communicatively coupled with a network 90 and/or a remote database 80, for example a local area network (LAN), hospital network, intranet, internet, "cloud" based network, computing device, electronic health record (EHR) system, combinations thereof, or the like. In an embodiment, the device 600 can be communicatively coupled with additional medical systems 70, for example ultrasound systems, fluid collection systems, automatic urine output systems, thoracic or other drainage systems, infusion systems, enteral feeding systems, ventilator and nebulizer systems, or the like. To note, the amount of fluid lost through respiration can be substantial. These additional medical systems 70 can provide additional information to the device 600 to determine volumes of fluid infused to, or evacuated from, the patient 10. The additional medical systems 70 can be directly coupled with the device 600, communicatively coupled, either wired or wirelessly, directly with the device 600, or communicatively coupled with the device 600 by way of one of the network 90 or the remote database 80.

In an embodiment, the device 600 can include a TBW logic 116B configured to measure an electrical impedance value for the patient and determine a TBW value using bio-impedance spectroscopy ("BIS"). As used herein, bio-impedance spectroscopy can also be termed bio-impedance plethysmography or bio-impedance tomography. To note, bio-impedance spectroscopy differs from bio-impedance analysis. Bio-impedance analysis relies on generalizations in patient body shape, size, age, height, weight, gender, ethnicity, and/or demographic. While these generalizations can be applicable to "normal" patients, such generalizations can be inapplicable to critical care patients. Further, critical care patients also require much higher accuracy in patient values. For example, HF patients maybe overweight due to excess body fluid resulting in fluid overload of the heart. As such, the generalizations relied on by BIA-based systems provide less accurate TBW or BV measurements. Further, HF patients require a much higher accuracy in TBW and BV measurements to provide faster confirmation that diuretic treatments are taking effect. If diuretic treatments were failing to take effect, then clinicians would need to quickly turn to alternative treatments.

In an exemplary method of use, a standing scale device 600 is provided, as described herein. A patient 10 can stand on the foot plate 620 and place a bare foot on each of the foot electrode sensors 602, for example a left foot on the left foot electrode 602A and a right foot on the right foot electrode 602B. In an embodiment, the patient 10 can also grasp the handle 622 with both hands, grasping a left hand electrode 604A with a bare left hand and grasping a right hand electrode 604B with a bare right hand. It is important to note that the patient contacts the electrodes 602, 604 with bare skin to provide an electrical contact therebetween.

An excitation signal can then be provided by a first electrode, e.g. one of the foot electrodes 602, or the hand electrodes 604. A second electrode can then detect the excitation signal. In an embodiment, the second electrode can be one of the foot electrodes 602, or the hand electrodes 604 that is different from the first electrode. For example, the excitation signal can be provided by the right foot electrode 602B, and detected by one of the left foot electrode 602A, left hand electrode 604A, right hand electrode 604B, or combinations thereof. In an embodiment, the excitation signal can be provided by one or more of the left foot electrode 602A, right foot electrode 602B, left hand electrode 604A, right hand electrode 604B, or combinations thereof. In an embodiment, the second, detecting electrode can be one or more of the left foot electrode 602A, right foot electrode 602B, left hand electrode 604A, right hand electrode 604B, or combinations thereof. It will be appreciated that these and other combinations of excitation and detection electrodes are also contemplated without limitation.

The TBW logic 116B can be configured to measure both the excitation signal provided at the first electrode, as well as detect the received excitation signal at the second electrode. The TBW logic 116B can then determine an electrical impedance value for the patient 10. The TBW logic 116B can then apply the electrical impedance value to a BIS model (e.g. a BV model 150 or TBW model) for the patient 10 to determine a TBW value for the patient 10. To note, a TBW model is used in a similar way to a BV model 150 (see FIGS. 10A-10C) except it is used to determine a TBW value for a patient instead of a BV value. The model converts an impedance value to a TBW value and can be modified by the system 600 as determined by the logic 116 to be personalized to the individual patient 10, as described herein.

In an embodiment, a first pair of electrodes can be configured to measure a TBW value using BIS, and a second pair of electrodes can be configured to measure a BV value using BIS. For example, a first pair of foot electrodes 602A, 602B can be configured to pass an excitation signal through the bladder 12 of the patient 10 to determine a BV value for the patient 600. A second pair of hand electrodes 604A, 604B, can be configured to pass an excitation signal through a torso region 14 of the patient 10 to determine a TBW measurement of the body tissues for the patient 10. Advantageously, the device 600 can determine a TBW value for the patient 10 and modify the BIS model to account for the TBW of the tissues surrounding the bladder 12. As such, the device 600 can determine an accurate BV measurement for the patient 10 without relying on assumptions in population or demographics. In an embodiment, second pair of hand electrodes 604A, 604B, can be configured to pass an excitation signal through a torso region 14 to determine a volume of fluid disposed in the lungs 16. As such, the device 600 can determine a volume of fluid disposed within the lungs 16 (i.e. a LFV value).

In an embodiment, the foot plate 620 can further include a pressure sensor configured to detect a pressure applied thereon when the patient 10 is standing on the foot plate 620. The TBW logic 116B can then determine a body weight value for the patient 10. In an embodiment, the TBW value, BV value, body weight value, LFV value or combinations thereof can be displayed to the clinician on a user interface 618. In an embodiment, the device 600 can further include a communications logic 116C configured to communicate one of the TBW value, BV value, body weight value, or LFV value to a network 90 and/or a remote database 80, e.g. an EHR system, or the like.

In an embodiment, additional information can be entered to the device 600 by way of the user interface 618, or provided by way of the remote database 80 or network 90. Exemplary variables can include, but not limited to, patient variables such as gender, age, height, weight, circumferential measurements, date/time of voiding events, urine output volumes, adjustments to automatic urine output volumes, or the like. These variables can be entered by the clinician, patient, or automatically queried from the remote database 80, by way of a network 90, e.g. Electronic Hospital Records, "cloud" based network, intranet, internet, LAN, or the like.

Figure 13:
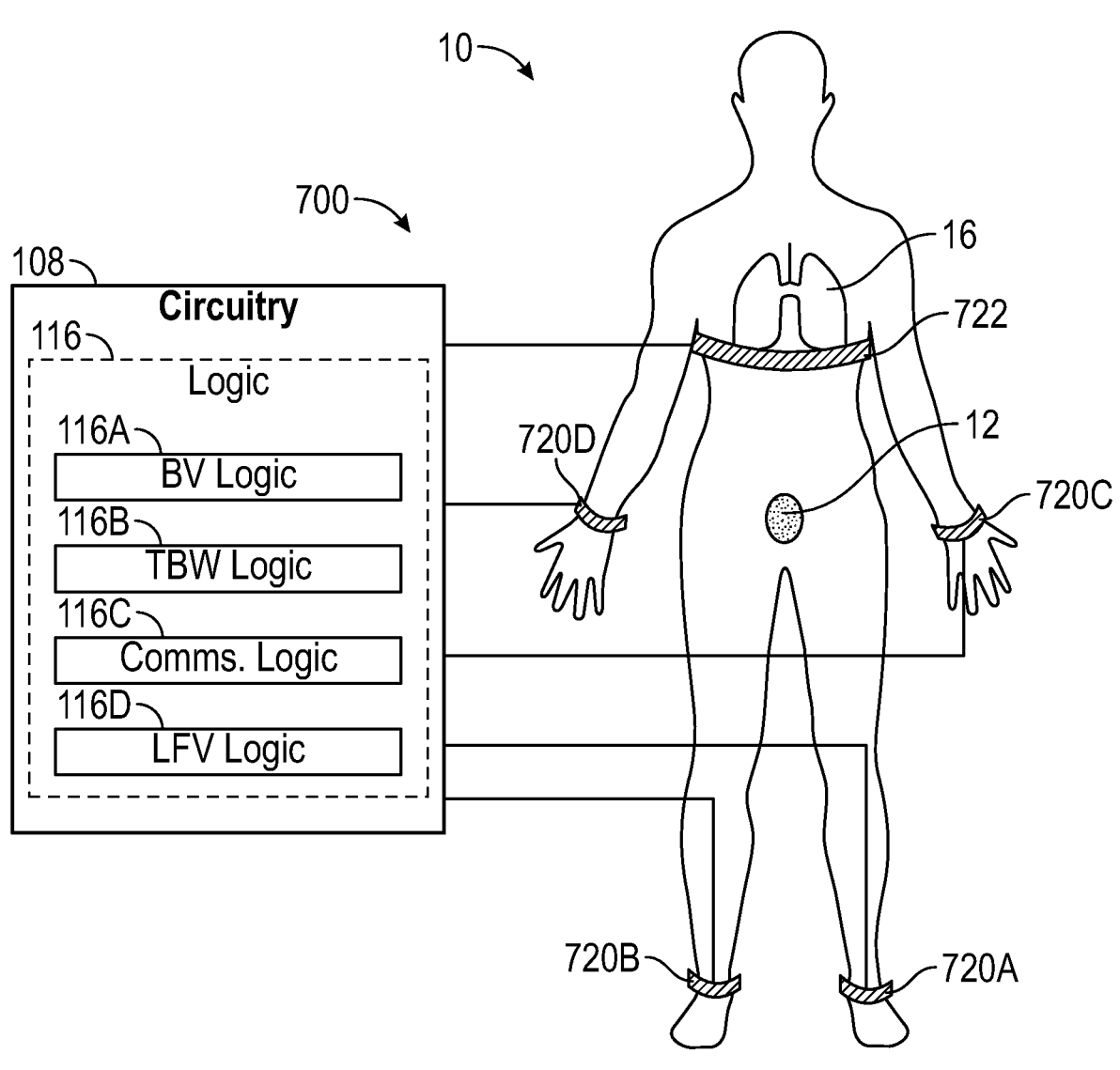
FIG. 13 shows a perspective view of a wearable, non-invasive TBW measuring device in an exemplary environment of use, in accordance with embodiments disclosed herein.
Figure 14A:
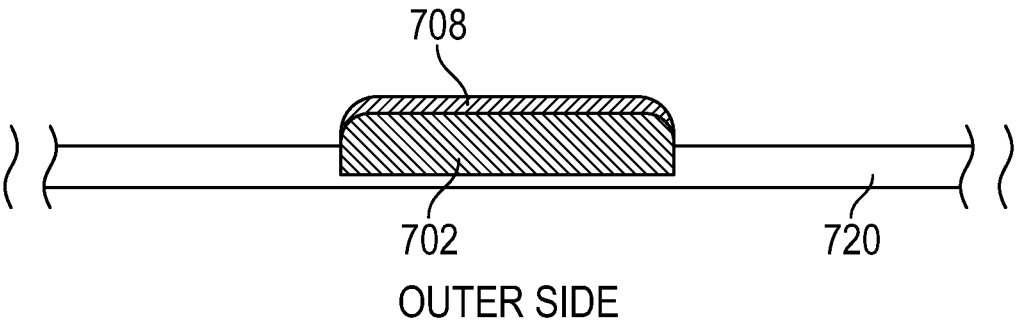
FIG. 14A shows a cross-section view of a sensor of the non-invasive TBW measuring device of FIG. 13, in accordance with embodiments disclosed herein.
Figure 14B:
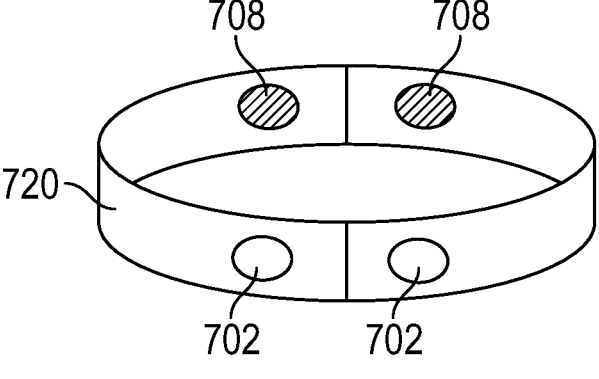
FIG. 14B shows a perspective view of a sensor and bracelet assembly the non-invasive TBW measuring device of FIG. 13, in accordance with embodiments disclosed herein.

As shown in FIGS. 13-14B, in an embodiment, a TBW device 700 is provided including circuitry 108, as described herein, that is communicatively coupled with a sensor 702 disposed on a bracelet 720. In an embodiment, the circuitry 108 can be contained within a single standalone unit, hand held computing device, or "base station" and communicatively coupled with the sensors 702 by either wired or wireless communication. The "base station" can be disposed proximate the patient, i.e. coupled to the patient's bed, or disposed within the same room. In an embodiment, the circuitry 108 can be carried by the patient 10 in a bag or pouch or "fanny pack," for example, the circuitry 108 can be disposed on a belt secured about the patient's torso.

In an embodiment, the sensor 702 can be an electrode configured to provide, or detect, an excitation signal. The sensor 702 can be disposed on a bracelet 720 configured to encircle a wrist or ankle portion of the patient 10 and support the electrode 702 against the skin surface of the patient 10. In an embodiment, the bracelet 720 can be adjustable or elasticated to fit different sized patients. In an embodiment, the bracelet 720 can include one or more markers to facilitate correct alignment of the electrode 702. For example, a marker can align with an anatomical fiduciary mark on the patient 10, such as an ankle bone or wrist bone to align the sensor correctly with the patient 10.

In an embodiment, the TBW device 700 can include a left foot bracelet 720A, a right foot bracelet 720B, a left hand bracelet 720C, a right hand bracelet 720D, or combinations thereof. In an embodiment, each of the bracelets 720A-720D can include a sensor 702. In an embodiment, each of the bracelets 720A-720D can include an array of sensors 702.

The sensor 702 can be communicatively coupled, either wired or wirelessly, with circuitry 108. The circuitry 108 can include logic 116, e.g. a BV logic 116A, TBW logic 116B, LFV logic 116D, etc. configured to provide and/or detect excitation signals and determine a BV value, TBW value, a LFV value for a patient 10 using BIS, as described herein. Advantageously, the bracelet(s) 720 and electrode sensor(s) 702 can worn by the patient 10 while the patient is in a prone or seated position, for example if the patient is bed-ridden and/or is unable to stand.

In an embodiment, as shown in FIG. 13, the device 700 can further include a chest strap 722 extending about a lung region 16 of the patient 10 and including one or more sensors 702 as described herein. The chest strap 722 and sensor 702 assembly can be communicatively coupled with a lung fluid volume ("LFV") logic 116D. The LFV logic 116D can be configured to measure an electrical impedance value for the lungs 16 of the patient and determine a volume of fluid disposed therein, i.e. LFV value. In an embodiment, the LFV logic 116D can use bio-impedance spectroscopy (BIS) to determine a volume of fluid within the lungs 16. In an embodiment, the device 700 can use the TBW value to compensate for fluid disposed in the tissues surrounding the lungs 16 to provide an accurate LFV value.

As shown in FIG. 14A, in an embodiment the sensor 702 can include an electrode having a coating 708 disposed on a surface thereof. The coating can be disposed between a surface of the electrode 702 and a skin surface of the patient 10. The coating 708 can include a hydrogel, urethane gel, or combinations thereof. The coating 708 can be configured to improve electrical contact between the electrode 702 and the skin surface of the patient 10. Advantageously, the electrode 702 with the coating 708 can require less pressure between the electrode 702 and the skin surface in order to maintain an electrical contact therebetween. As such, the electrodes can be worn for a long period of time without discomfort.

In an embodiment, the coating 708 can include a pressure-reactive adhesive configured to hold the electrode against the skin surface of the patient 10. Advantageously, the adhesive allows the electrode 702 to be secured to the patient 10 without the need for a bracelet 720. The pressure from a bracelet 720, may become uncomfortable for the patient over extended periods of time and can lead to increased risk for skin infection, dermatitis, and skin breakdown.

Advantageously, the device 700 can worn by the patient 10 for an extended period of time and can periodically measure impedance levels to determine changes in TBW values, BV values, or LFV values for the patient 10. As such, embodiments described herein can provide time-based BV, TBW, or LFV data. Such time-based BV, TBW, or LFV data can be communicated with networks 90 or remote databases 80 and can be important in quickly determining if treatments are taking an effect, e.g. diuretic treatments on HF patients.

Advantageously, embodiments disclosed herein can use BIS to determine a TBW value, BV value, and/or LFV value for the patient. In contrast with bio-impedance analysis ("BIA") systems that rely on assumptions in age, gender, and other demographics, BIS systems can adapt to each patient, accounting for "abnormal" conditions, and provide accurate TBW, BV, LFV data. As such, accurate TBW values can be determined for all patients with differing body compositions.

Advantageously, embodiments disclosed herein can be integrated into the clinicians existing work flow and communicatively coupled to a network 80 and/or remote database 90, e.g. EHR, or the like. As such TBW and/or BV measurements can be determined by the device and communicated to the EHR in real-time without any extra work or inconvenience to the clinician or the patient. This can provide accurate and immediate information on TBW, BV, and/or LFV values to determine the efficacy of diuretics or other therapies. Further, this can reduce the clinician's workload and mitigate data entry mistakes.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A system for measuring a volume of fluid within a bladder of a patient, comprising:
   a bladder volume monitoring (BVM) system including an impedance sensor contacting a skin surface of the patient, the bladder volume monitoring system configured to measure an electrical impedance of a bladder portion of the patient and determine a bladder volume value for the patient using a model, wherein the bladder volume value is an estimated volume of fluid within the bladder;
   a BVM training system configured to receive one or more urine output values for a volume of fluid voided from the bladder and including a logic configured to determine a difference between the bladder volume value and a urine output value of the one or more urine output values and iteratively modify the model to reduce the difference between the bladder volume value and the urine output value to improve accuracy of the model; and
   a bladder training system including a flow sensor and a valve, the flow sensor coupled with one of a catheter, a drainage tube, or a collection container, the valve configured to control a flow of fluid voided from the bladder, to train the bladder of the patient to a natural bladder cycle, the bladder training system configured to determine a urine output value of the one or more urine output values.

2. The system according to claim 1, wherein the bladder volume monitoring system uses one of bio-impedance analysis, bio-impedance spectroscopy, bio-impedance plethysmography, or bio-impedance tomography to determine the bladder volume value.

3. The system according to claim 1, wherein the bladder volume monitoring system is configured to measure a first electrical impedance value before a voiding event and a second electrical impedance value after the voiding event to determine the bladder volume value.

4. The system according to claim 1, wherein the impedance sensor includes a first sensor array having a first electrode configured to provide an excitation signal and a second electrode configured to measure an electric impedance of the excitation signal through the bladder portion of the patient.

5. The system according to claim 1, wherein the bladder volume monitoring system further includes a second sensor array including a third electrode configured to provide a second excitation signal and a fourth electrode configured to measure a second electric impedance of the second excitation signal through a second portion of the patient to determine a total body water value for the patient.

6. The system according to claim 5, wherein the logic retrieves the total body water value and further modifies the model to reduce the difference between the bladder volume value and the urine output value to improve accuracy of the model.

7. The system according to claim 1, wherein the impedance sensor is disposed on a belt secured about a patient's waist and configured to align the impedance sensor with the bladder portion of the patient.

8. The system according to claim 1, further including an accelerometer or a gyroscope configured to detect a movement or a position of the patient, the logic configured to receive a signal from one of the accelerometer or the gyroscope and modify the model to improve accuracy of the bladder volume value for the patient.

9. The system according to claim 1, further including an electromyography sensor in contact with the skin surface of the patient and configured to detect one of a contraction of a detrusor muscle, or a relaxation of a urinary sphincter of the patient to determine an occurrence of a bladder voiding event.

10. The system according to claim 1, wherein the system is communicatively coupled with one of a network, a remote database, an intranet, an internet, a cloud-based network, or an electronic health record system.

11. The system according to claim 1, wherein the impedance sensor is in wireless communication with the bladder volume monitoring system, and wherein one of the bladder volume monitoring system, the training system, or the logic are disposed within a stand-alone unit.

12. The system according to claim 11, wherein the stand-alone unit is selected from the group consisting of a base station, a portable computing device, a monitor, a handheld device, a wearable device, a smart watch, a laptop, and a tablet device.

13. The system according to claim 1, wherein the training system further includes one or both of an ultrasound training system and a pressure-based training system, each configured to provide a urine output value of the one or more urine output values.

14. A bladder volume measuring system, comprising:

a first sensor array including an electrode in contact with a skin surface of a patient, the first sensor array configured to determine an electrical impedance value of a bladder of the patient;

an ultrasound system including a transducer in contact with the skin surface of the patient, the ultrasound system configured to determine a volume of fluid within the bladder of the patient; and a bladder volume monitoring system including logic configured to determine the volume of fluid within the bladder from the electrical impedance value using a bladder volume model, and configured to iteratively verify the bladder volume model with the volume of fluid within the bladder as determined by the ultrasound system.

15. The bladder volume measuring system according to claim 14, wherein one of the first sensor array or the transducer are disposed on a belt configured to encircle a waist portion of the patient and secure one of the first sensor array or the transducer to the skin surface of the patient.

16. The bladder volume measuring system according to claim 14, wherein the bladder volume monitoring system uses one of bio-impedance analysis, bio-impedance spectroscopy, bio-impedance plethysmography, or bio-impedance tomography to determine the volume of fluid within the bladder from the electrical impedance value.

17. The bladder volume measuring system according to claim 14, wherein the first sensor array includes a first electrode configured to provide an excitation signal and a second electrode configured to measure an electric impedance of the excitation signal through the bladder of the patient.

18. The bladder volume measuring system according to claim 14, wherein the bladder volume monitoring system further includes a second sensor array including a third electrode configured to provide a second excitation signal and a fourth electrode configured to measure a second electric impedance of the second excitation signal through a second portion of the patient to determine a total body water value for the patient.

19. The bladder volume measuring system according to claim 18, wherein the bladder volume monitoring system logic retrieves the total body water value and modifies the bladder volume model to improve accuracy of the bladder volume model for the patient.

20. The bladder volume measuring system according to claim 14, further including an accelerometer or a gyroscope configured to detect a movement or position of the patient, the bladder volume monitoring system logic configured to receive a signal from one of the accelerometer or the gyroscope and modify the bladder volume model to improve accuracy of the bladder volume model for the patient.

21. The bladder volume measuring system according to claim 14, further including an electromyography sensor in contact with a skin surface of the patient and configured to detect one of a contraction of a detrusor muscle or a relaxation of a urinary sphincter of the patient to determine an occurrence of a bladder voiding event.

22. The bladder volume measuring system according to claim 14, wherein the logic of the bladder volume monitoring system is communicatively coupled with one of a network, a remote database, an intranet, an internet, a cloud-based network, or an electronic health record system.

23. The bladder volume measuring system according to claim 14, wherein the first sensor array is in wireless communication with the bladder volume monitoring system, and wherein one of the bladder volume monitoring system or the ultrasound system are disposed within a stand-alone unit.

24. The bladder volume measuring system according to claim 23, wherein the stand-alone unit is selected from the group consisting of a base station, a portable computing device, a monitor, a handheld device, a wearable device, a smart watch, a laptop, and a tablet device.

25. The bladder volume measuring system according to claim 14, further including a user interface configured to receive a voided fluid volume input.

\* \* \* \* \*